United States Patent
Snow

(10) Patent No.: US 9,392,998 B2
(45) Date of Patent: Jul. 19, 2016

(54) IMPACT BIOPSY DEVICE AND METHOD OF USE

(71) Applicant: Merit Medical Systems, Inc., South Jordan, UT (US)

(72) Inventor: Jeremy W. Snow, South Jordan, UT (US)

(73) Assignee: Merit Medical Systems, Inc., South Jordan, UT (US)

( * ) Notice: Subject to any disclaimer, the term of this patent is extended or adjusted under 35 U.S.C. 154(b) by 236 days.

(21) Appl. No.: 14/157,935

(22) Filed: Jan. 17, 2014

(65) Prior Publication Data

US 2014/0207021 A1 Jul. 24, 2014

Related U.S. Application Data

(60) Provisional application No. 61/754,401, filed on Jan. 18, 2013.

(51) Int. Cl.
*A61B 10/02* (2006.01)

(52) U.S. Cl.
CPC .................................. *A61B 10/0266* (2013.01)

(58) Field of Classification Search
CPC ........... A61B 10/0233; A61B 10/0241; A61B 10/0266; A61B 10/0275
USPC .................................................. 600/564–567
See application file for complete search history.

(56) References Cited

U.S. PATENT DOCUMENTS

| | | | |
|---|---|---|---|
| 5,172,702 A | 12/1992 | Leigh et al. | |
| 5,419,641 A | 5/1995 | Fujinami et al. | |
| 5,601,572 A | 2/1997 | Middleman et al. | |
| 5,655,542 A | 8/1997 | Weilandt | |
| 5,788,651 A | 8/1998 | Weilandt | |
| 5,800,389 A | 9/1998 | Burney et al. | |
| 5,842,999 A * | 12/1998 | Pruitt ................. | A61B 10/0275 600/562 |
| D418,223 S | 12/1999 | Phipps et al. | |
| D428,150 S | 7/2000 | Ruf et al. | |
| 6,126,617 A | 10/2000 | Weilandt et al. | |
| 6,196,978 B1 | 3/2001 | Weilandt et al. | |
| 6,322,523 B2 | 11/2001 | Weilandt et al. | |
| D457,955 S | 5/2002 | Bilitz | |
| D463,555 S | 9/2002 | Etter et al. | |
| 6,488,662 B2 | 12/2002 | Sirimanne | |

(Continued)

FOREIGN PATENT DOCUMENTS

| AT | 366546 | 6/1976 |
|---|---|---|
| EP | 0966920 | 12/1999 |

(Continued)

OTHER PUBLICATIONS

International Search Report and Written Opinion dated Apr. 30, 2015 for PCT/US2015/012002.

(Continued)

*Primary Examiner* — Michael C Stout
(74) *Attorney, Agent, or Firm* — Stoel Rives LLP

(57) ABSTRACT

An impact biopsy device is disclosed. The impact biopsy device may be configured to displace various cutting elements, such as an outer tubular member and cutting element and a cannula to sever a tissue sample from a patient. The impact biopsy device may comprise an actuation system configured to transfer displacement or force to the cutting elements by the impact of an element on another element.

26 Claims, 16 Drawing Sheets

(56) References Cited

U.S. PATENT DOCUMENTS

| | | |
|---|---|---|
| 6,497,687 B1 | 12/2002 | Blanco |
| D490,152 S | 5/2004 | Myall et al. |
| 7,041,065 B2 | 5/2006 | Weilandt et al. |
| 7,247,160 B2 | 7/2007 | Seiler et al. |
| D571,009 S | 6/2008 | Smith et al. |
| D586,916 S | 2/2009 | Faulkner et al. |
| D598,543 S | 8/2009 | Vogel et al. |
| 7,608,048 B2 | 10/2009 | Goldenberg |
| D612,044 S | 3/2010 | Scheibe |
| D612,051 S | 3/2010 | Ruf |
| D619,251 S | 7/2010 | Justiniano-Garcia et al. |
| D628,293 S | 11/2010 | Ruf |
| 8,137,317 B2 | 3/2012 | Osypka |
| 2001/0009979 A1 | 7/2001 | Weilandt et al. |
| 2004/0133124 A1 | 7/2004 | Bates et al. |
| 2004/0215103 A1 | 10/2004 | Mueller, Jr. et al. |
| 2005/0054947 A1 | 3/2005 | Goldenberg |
| 2005/0125017 A1 | 6/2005 | Kudrna et al. |
| 2006/0085019 A1 | 4/2006 | Cote et al. |
| 2007/0027407 A1 | 2/2007 | Miller |
| 2007/0078472 A1 | 4/2007 | Singh |
| 2007/0142744 A1 | 6/2007 | Provencher |
| 2007/0179403 A1 | 8/2007 | Heske et al. |
| 2007/0250037 A1 | 10/2007 | Brimhall et al. |
| 2008/0200833 A1* | 8/2008 | Hardin .............. A61B 10/0275 600/566 |
| 2008/0228104 A1* | 9/2008 | Uber .................. A61B 10/0233 600/567 |
| 2008/0281223 A1 | 11/2008 | Goldenberg |
| 2008/0300507 A1 | 12/2008 | Figueredo et al. |
| 2009/0143698 A1 | 6/2009 | Janssens |
| 2009/0299220 A1* | 12/2009 | Field .................. A61B 10/0275 600/567 |
| 2010/0130887 A1 | 5/2010 | Selis |
| 2010/0168773 A1 | 7/2010 | Funderburk et al. |
| 2011/0251631 A1 | 10/2011 | Trees et al. |
| 2012/0220894 A1 | 8/2012 | Melsheimer |
| 2013/0131548 A1 | 5/2013 | McGhit et al. |
| 2014/0171826 A1 | 6/2014 | Lampropoulos et al. |
| 2015/0045828 A1 | 2/2015 | McArthur et al. |
| 2015/0094751 A1 | 4/2015 | Chen et al. |

FOREIGN PATENT DOCUMENTS

| | | |
|---|---|---|
| WO | WO96/22733 | 8/1996 |
| WO | WO99/44505 | 9/1999 |
| WO | WO2006/013389 | 2/2006 |
| WO | 2012167216 A2 | 12/2012 |

OTHER PUBLICATIONS

International Search Report and Written Opinion dated Jan. 16, 2015 for PCT/US2015/011746.

Shuttle® and CT-Core® Semi-Automatic devices; Updated to the website between Nov. 8, 2012-Jan. 24, 2013. Accessed website on Jun. 27, 2014 at http://www.vigeohealthcare.com/gb/int_radiplogy.html.

International Search Report and Written Opinion dated May 1, 2014 for PCT/US2014/012043.

International Search Report and Written Opinion dated Apr. 3, 2014 for PCT/US2013/076418.

U.S. Appl. No. 14/598,457, filed Jun. 16, 2015, Snow.

U.S. Appl. No. 14/600,660, filed Jan. 20, 2015, Snow.

International Search Report and Written Opinion dated Jun. 23, 2015 for PCT/US2013/076418.

Office Action dated Jun. 1, 2016 for U.S. Appl. No. 14/134,280.

* cited by examiner

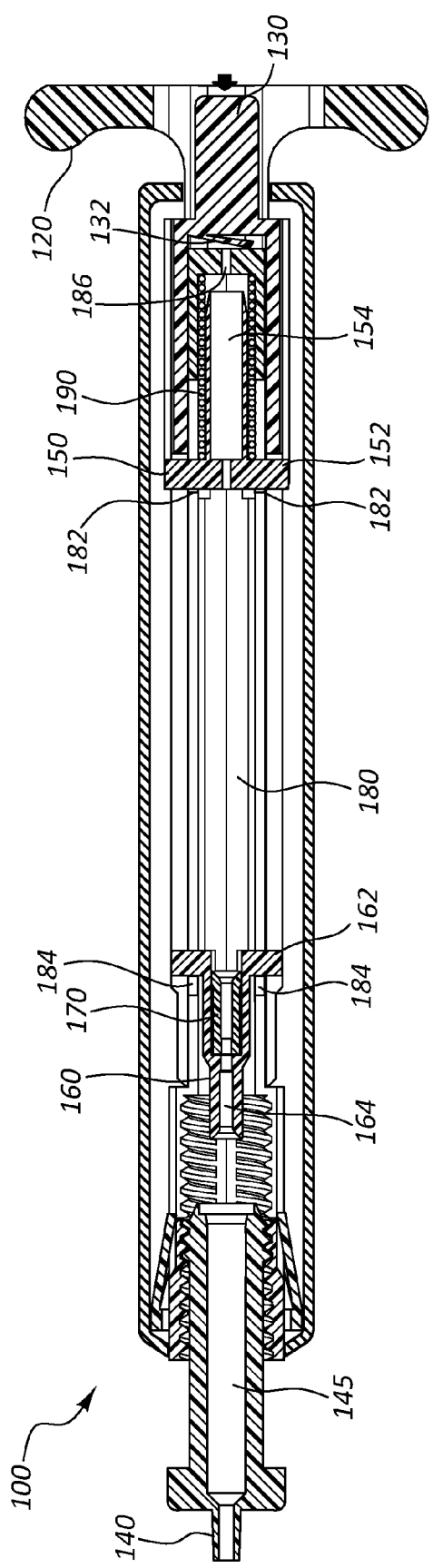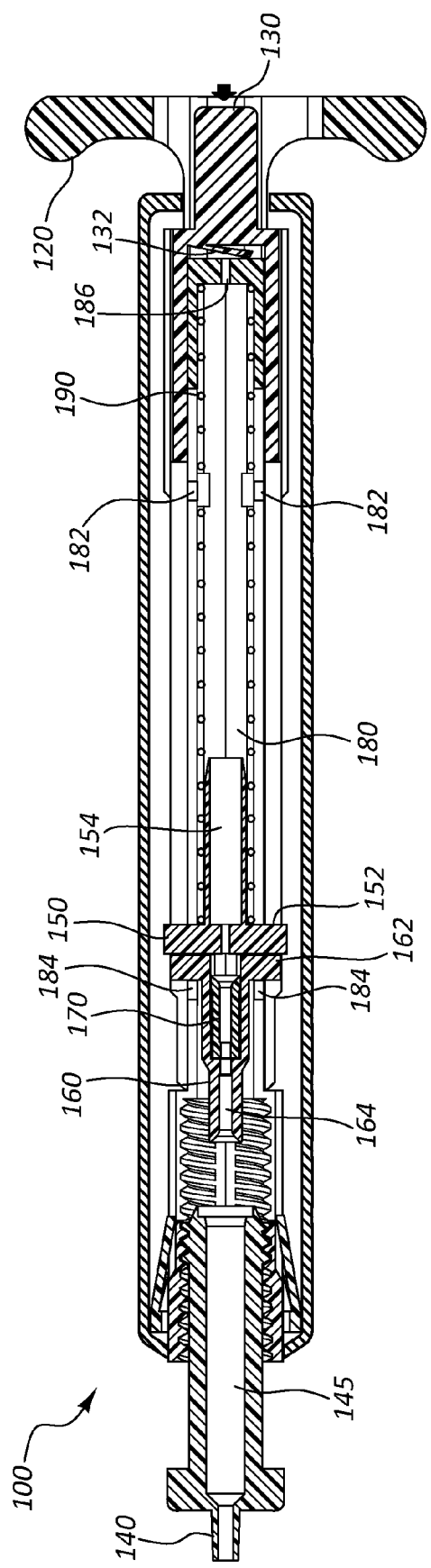

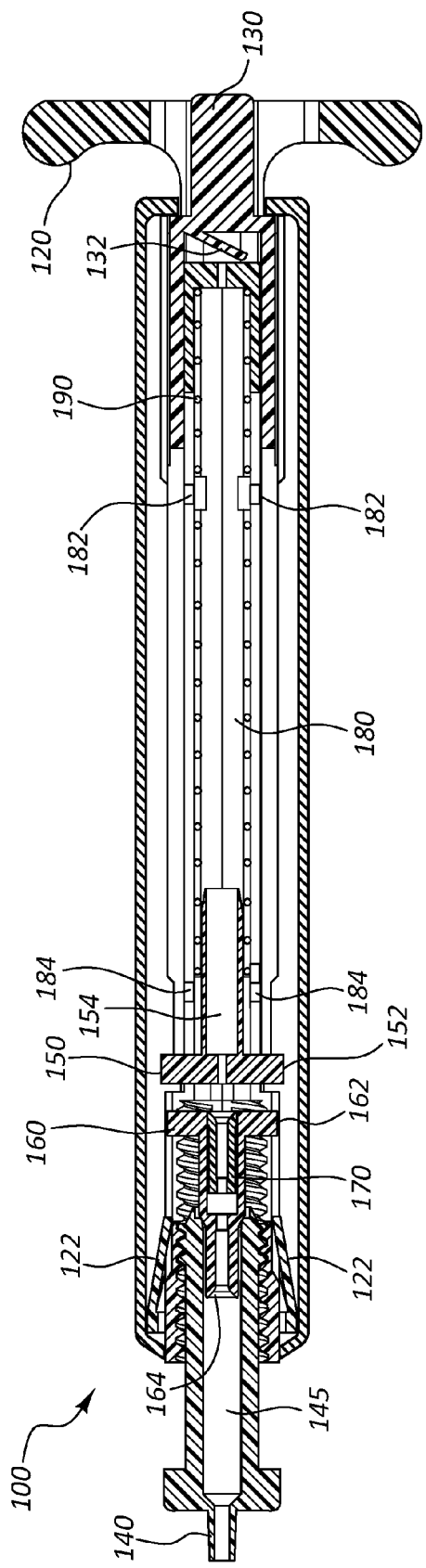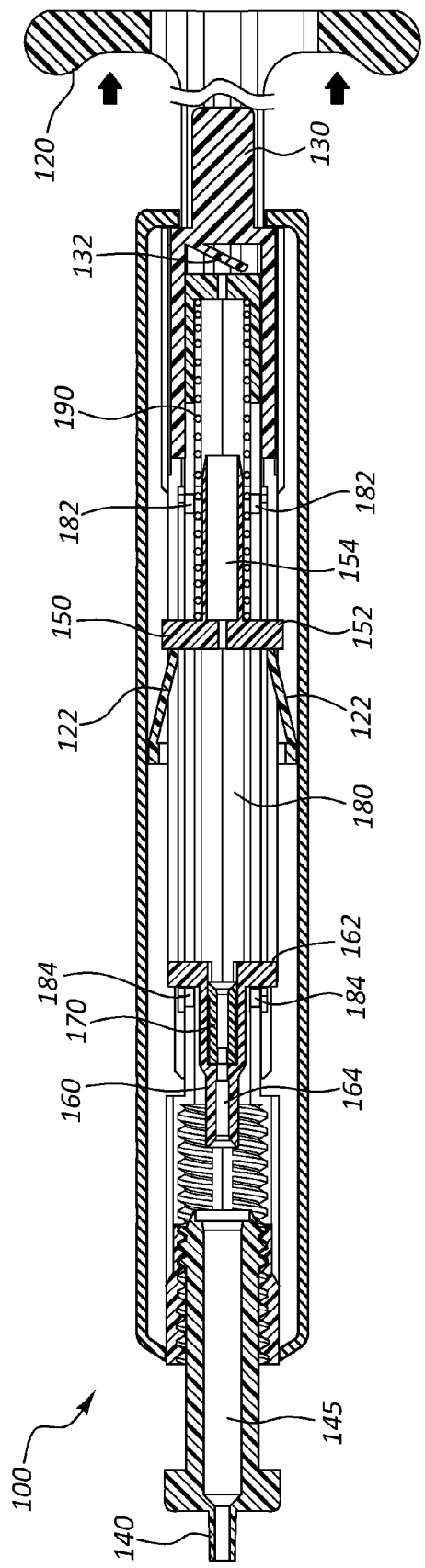
FIG. 5E
FIG. 5F

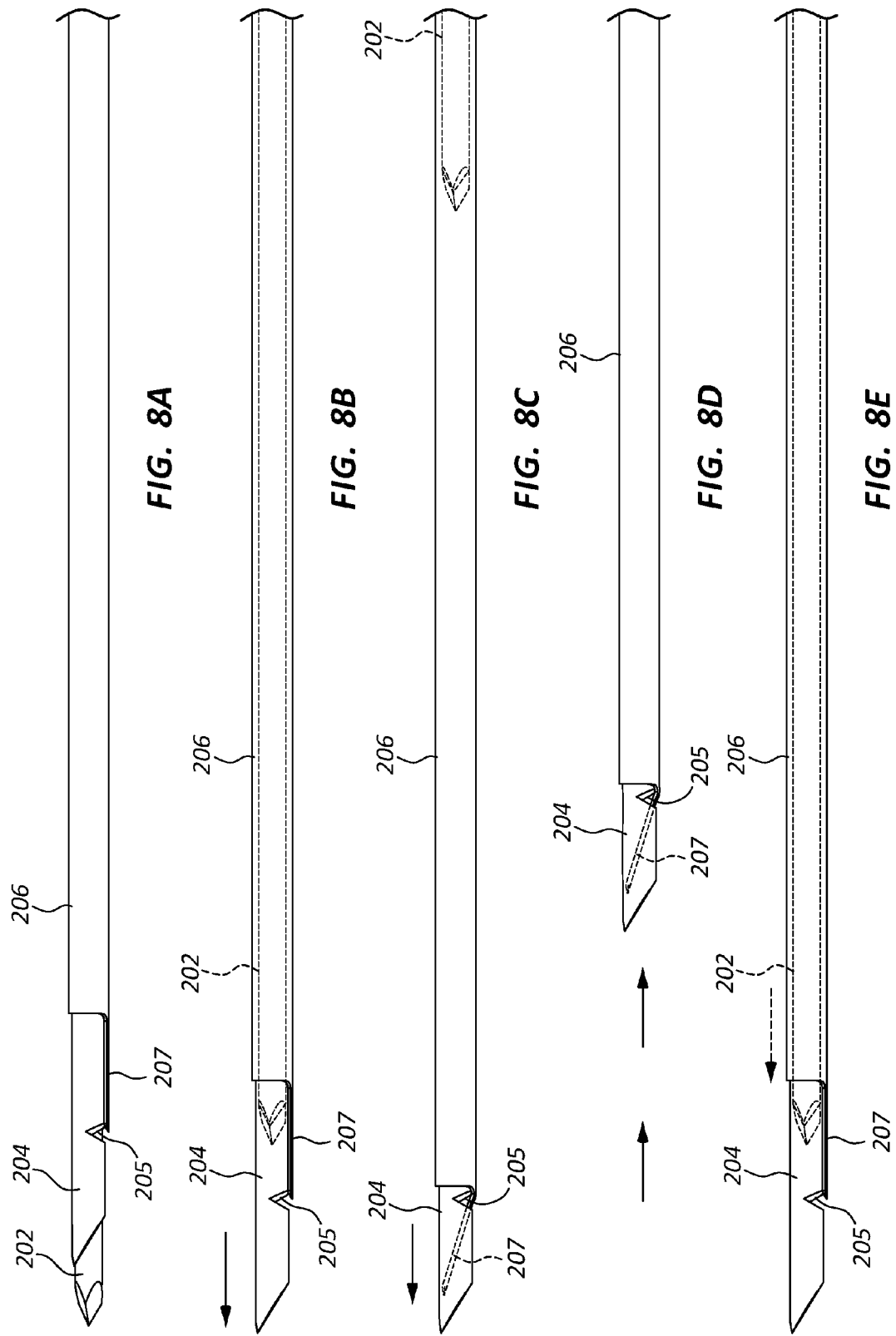

IMPACT BIOPSY DEVICE AND METHOD OF USE

RELATED APPLICATIONS

This application claims priority to U.S. Provisional Application No. 61/754,401 filed on Jan. 18, 2013 and titled "Impact Biopsy Device and Method of Use," which is hereby incorporated by reference in its entirety.

TECHNICAL FIELD

The present disclosure relates generally to medical devices. More specifically, the present disclosure relates to biopsy devices, including biopsy devices configured with an impact driven or kinetic energy operation system.

BRIEF DESCRIPTION OF THE DRAWINGS

The embodiments disclosed herein will become more fully apparent from the following description and appended claims, taken in conjunction with the accompanying drawings. The drawings depict only typical embodiments, which embodiments will be described with additional specificity and detail in connection with the drawings in which:

FIG. 5C is a cross-sectional view of the impact biopsy device of FIG. 1 in a third configuration.

FIG. 5D is a cross-sectional view of the impact biopsy device of FIG. 1 in a fourth configuration.

FIG. 5E is a cross-sectional view of the impact biopsy device of FIG. 1 in a fifth configuration.

FIG. 5F is a cross-sectional view of the impact biopsy device of FIG. 1 in a sixth configuration.

FIG. 8A is a side view of a portion of the impact biopsy device of FIG. 7 in a first configuration.

FIG. 8B is a side view of a portion of the impact biopsy device of FIG. 7 in a second configuration.

FIG. 8C is a side view of a portion of the impact biopsy device of FIG. 7 in a third configuration.

FIG. 8D is a side view of a portion of the impact biopsy device of FIG. 7 in a fourth configuration.

FIG. 8E is a side view of a portion of the impact biopsy device of FIG. 7 in a fifth configuration.

DETAILED DESCRIPTION

Figure 1:
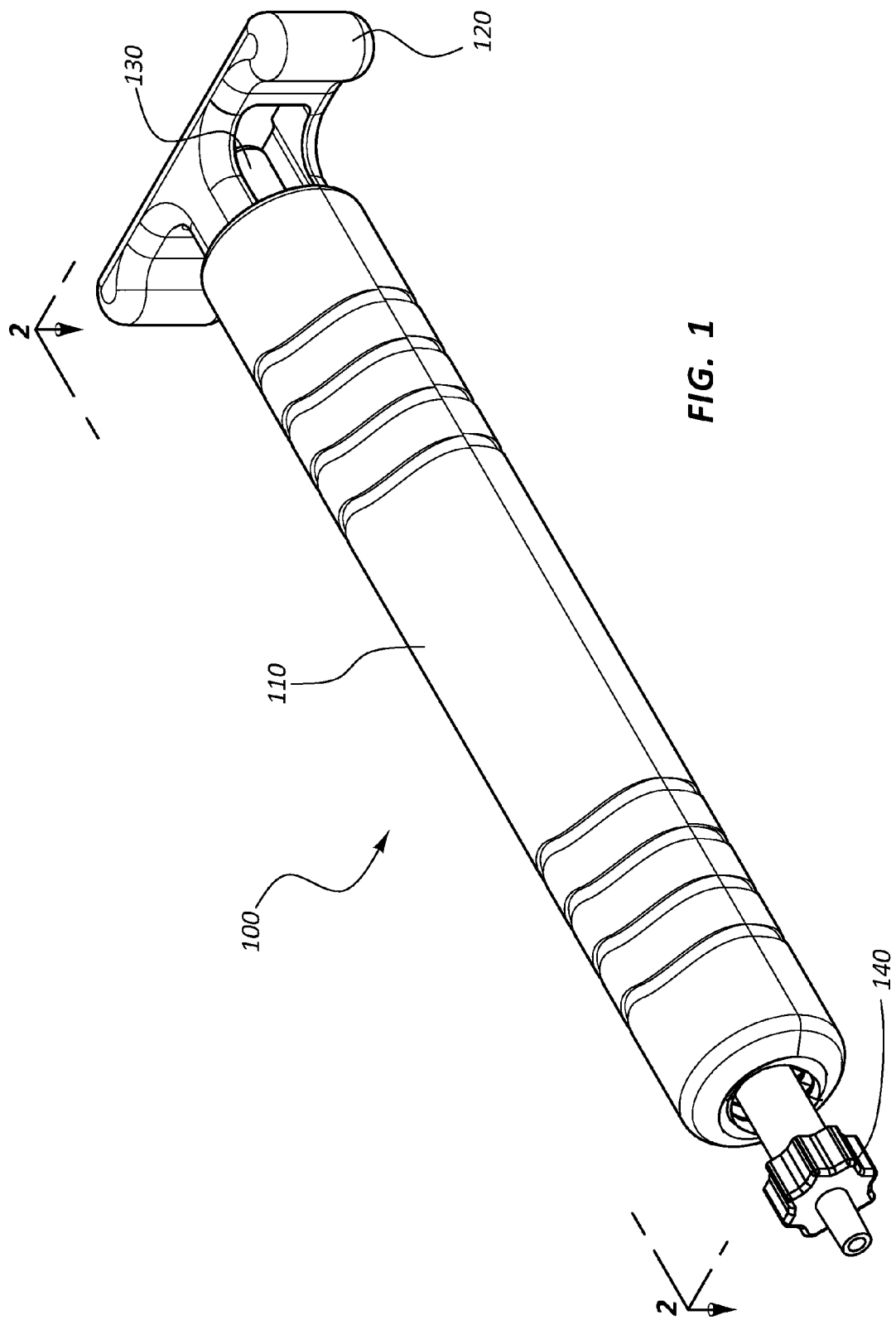
FIG. 1 is a perspective view of an impact biopsy device in a primed configuration.

Biopsy devices may be configured to retrieve tissue samples from various locations within a patient's body. For example, a biopsy device may comprise a needle assembly including cannula or other cutting members configured to sever a tissue sample. The needle assembly may be advanced to a location within the body through the skin of the patient (percutaneous access) or may be advanced through a body lumen or other structure.

Furthermore, a biopsy device may comprise an actuation mechanism configured to displace the needle assembly such that the needle assembly severs the targeted tissue sample. Biasing mechanisms such as springs, triggers, and so forth may be configured to allow a practitioner to manipulate various components of a needle assembly through manipulating the actuation mechanism. In addition to mechanical biasing mechanisms such as springs, compressed gas or other energy sources may be configured to power a biopsy device. In some embodiments, for example, a compressed $CO_2$ cartridge may be used to power a biopsy device.

Regardless of the energy source, a mechanism may be configured such that, once the needle assembly is disposed adjacent tissue to be biopsied, actuation of a single trigger may cause various components of a needle assembly to be displaced to sever a tissue sample. Biasing elements or other energy sources within the actuation mechanism may provide the force required to advance the needle assembly components, and other mechanisms may control the relative displacement of individual components of a needle assembly.

As further disclosed below, a biopsy device may comprise components configured to actuate the biopsy device through transfer of kinetic energy between components, including instances where one or more components are displaced due to an impact force.

It will be readily understood that the components of the embodiments as generally described and illustrated in the Figures herein could be arranged and designed in a wide variety of different configurations. Thus, the following more detailed description of various embodiments, as represented in the Figures, is not intended to limit the scope of the disclosure, but is merely representative of various embodiments. While the various aspects of the embodiments are presented in drawings, the drawings are not necessarily drawn to scale unless specifically indicated.

The phrases "connected to" and "coupled to" refer to any form of interaction between two or more entities, including mechanical, electrical, magnetic, electromagnetic, fluid, and thermal interaction. Two components may be coupled to each other even though they are not in direct contact with each other. For example, two components may be coupled to each other through an intermediate component.

The directional terms "proximal" and "distal" are used herein to refer to opposite locations on a medical device. The proximal end of the device is defined as the end of the device closest to the practitioner when the device is in use by the practitioner. The distal end is the end opposite the proximal end, along the longitudinal direction of the device, or the end furthest from the practitioner.

FIG. 1 is a perspective view of an impact biopsy device 100 in a primed configuration. The biopsy device 100 may comprise a body member 110 that may be configured to be grasped by a practitioner when the biopsy device 100 is in use. Thus, in some embodiments the body member 110 may comprise a handle. The biopsy device 100 may also comprise a priming handle 120. As further discussed below, displacement of the priming handle 120 with respect to the body member 110 may be configured to prime the biopsy device 100. Similarly, the biopsy device 100 may comprise an actuator, such as a trigger 130. Displacement of the trigger 130 with respect to the body member 110 may be configured to actuate elements within the body member 110, such as components of an actuation assembly, in connection with obtaining a tissue sample.

Additionally, the biopsy device 100 may comprise an adjustable stop 140. Displacement of the adjustable stop 140 with respect to the body member 110 may be configured to adjust or control the length of the tissue sample severed by the biopsy device 100.

Figure 2:
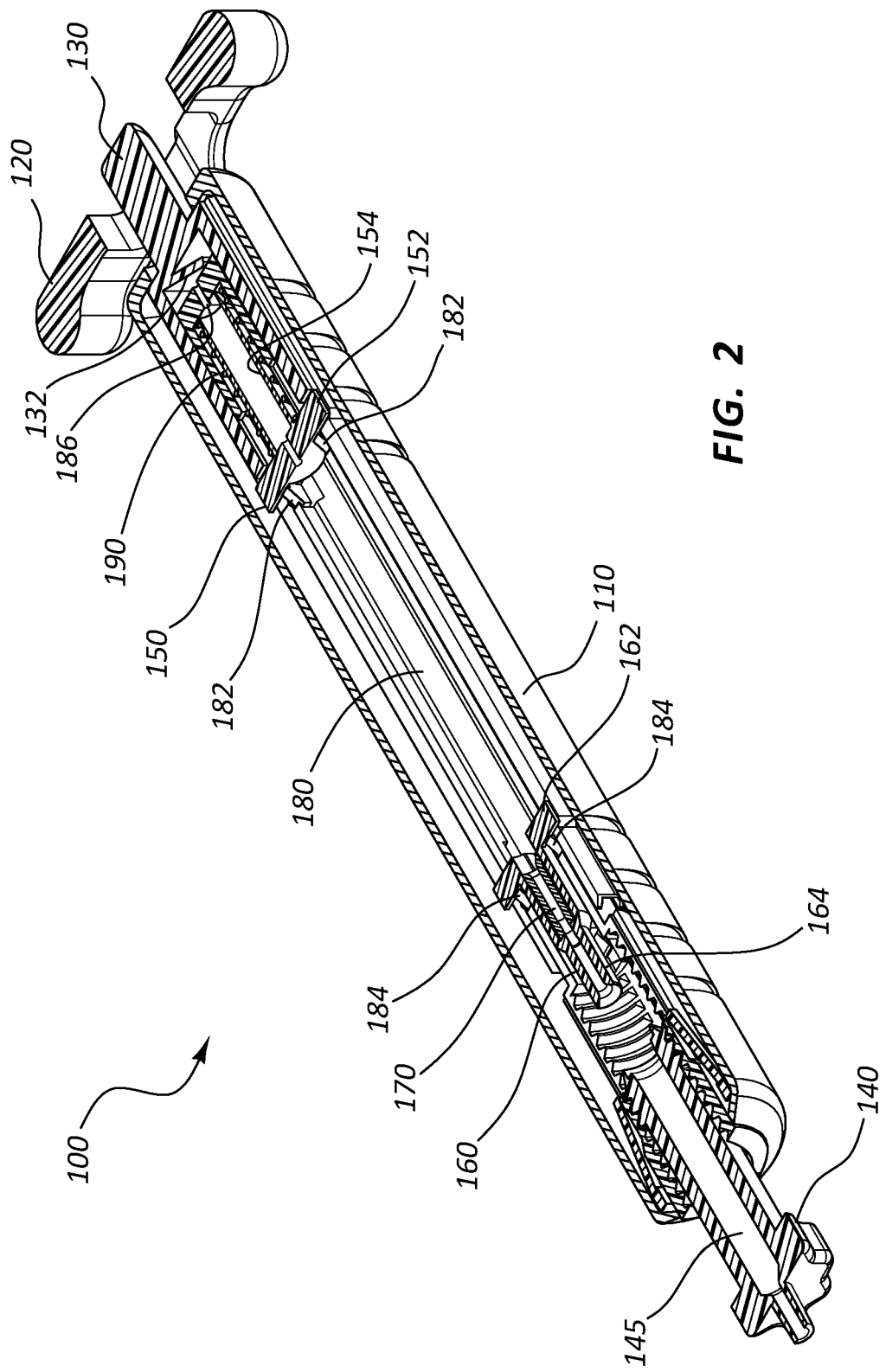
FIG. 2 is a cross-sectional view of the impact biopsy device of FIG. 1.

FIG. 2 is a cross-sectional view of the impact biopsy device 100 of FIG. 1. As shown in FIG. 2, the biopsy device 100 may include an actuation assembly comprised of components configured to displace a needle assembly or other cutting members. As used herein the actuation assembly refers generally to components configured to transfer energy to cutting members coupled to the biopsy device 100.

In the embodiment of FIGS. 1 and 2, no cutting members are coupled to the biopsy device 100. It is within the scope of this disclosure to couple any variety of needles, cannula, trocars, stylets, or other instruments to the biopsy device 100. For example, a stylet and cannula configured to sever a partial core tissue sample may be operably coupled to the biopsy device 100. Further, one or more cannula configured to obtain a full core tissue sample may be operably coupled to the biopsy device 100. In some embodiments, one or more elements of a needle or cutting assembly may be coupled to components within the body member 110 of the biopsy device 100 and may extend from the body member 110 through an adjustable stop lumen 145.

In the embodiment of FIGS. 1 and 2, the biopsy device 100 is disposed in a primed configuration, meaning the biopsy device 100 is disposed in a configuration from which it can be actuated. For example, the biopsy device 100 may comprise a biasing element, such as a spring 190. In the primed configuration, the spring 190 may be loaded such that potential energy is stored within the spring 190. When in the primed configuration, the biopsy device 100 is ready to be actuated. The biopsy device 100 may comprise a second biasing element, such as a trigger return spring 132, as further detailed below.

The biopsy device 100 may comprise a traveler 150 disposed within the body member 110. In the illustrated embodiment, the spring 190 is disposed around a shaft 154 of the traveler 150. In the primed configuration shown in FIG. 2, the traveler 150 may be disposed such that the spring 190 exerts a force on the traveler 150. In other words, the traveler 150 may be positioned such that the position of the traveler 150 compresses or loads the spring 190 between a flange 152 of the traveler 150 and a load surface 186 of a retention tube 180. Proximal catches 182 of the retention tube 180 may contact the flange 152 of the traveler 150 such that the proximal catches 182 maintain the position of the traveler 150 with respect to the retention tube 180 when the biopsy device 100 is in the primed configuration. Thus, in the configuration of FIG. 2, the spring 190 may exert a distally oriented force on the flange 152 of the traveler 150 that, in turn, exerts a distally oriented force on the proximal catches 182. A proximally oriented force, exerted on traveler flange 152 by the proximal catches 182, maintains the relative position of the traveler 150 with respect to the retention tube 180. In some embodiments, the retention tube 180 may be fixedly coupled to the body member 110, including embodiments wherein the retention tube 180 and body member 110 are integrally formed as a single part.

The embodiment of FIG. 2 further comprises an impact member 160 that may have a flange 162 and an extension 164. Distal catches 184 of the retention tube 180 may contact the impact member flange 162 preventing the impact member 160 from being displaced in a distal direction. A follower 170 may be coupled to the impact member 160 such that distal displacement of the impact member 160 causes distal displacement of the follower 170. As further described herein, the impact member 160 and follower 170 may each be coupled to cutting components configured to extend through the adjustable stop lumen 145 such that displacement of the impact member 160 and follower 170 displace the coupled cutting components.

Figure 3:
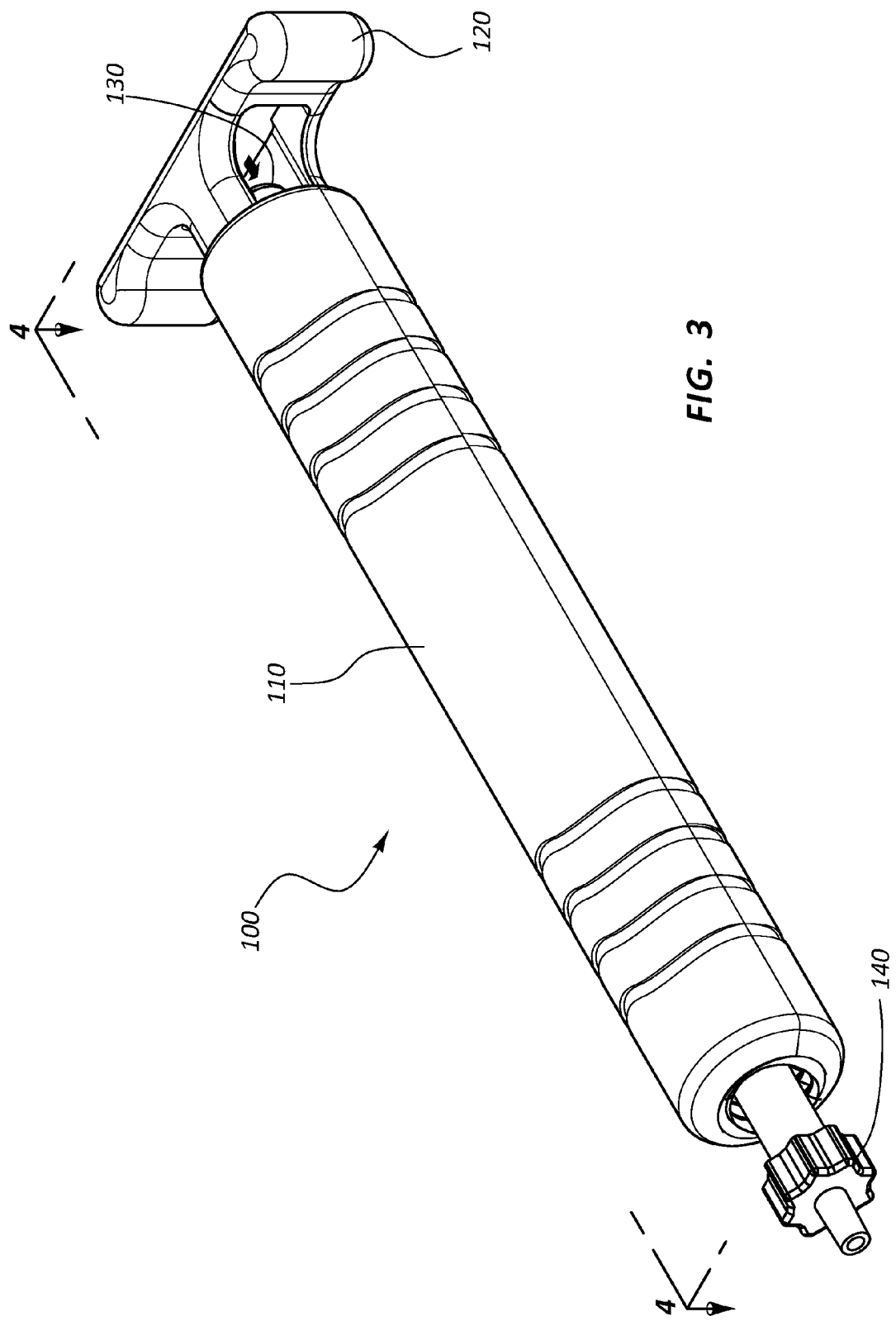
FIG. 3 is a perspective view of the impact biopsy device of FIG. 1 in an actuated configuration.
Figure 4:
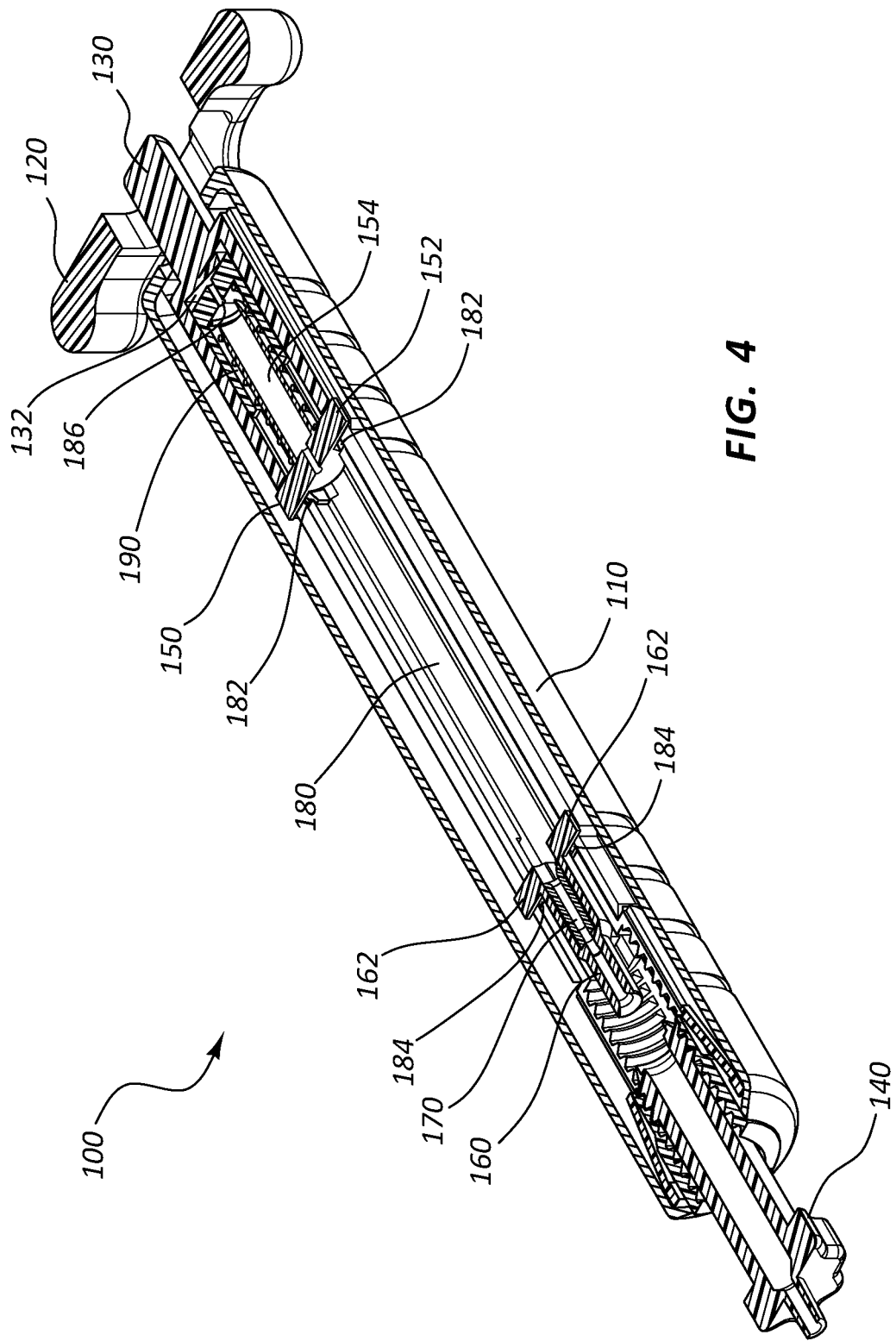
FIG. 4 is a cross-sectional view of the impact biopsy device of FIG. 3, in the configuration of FIG. 3.

FIG. 3 is a perspective view of the impact biopsy device 100 of FIG. 1 in an actuated configuration. FIG. 4 is a cross-sectional view of the impact biopsy device 100 of FIG. 3, in the same actuated configuration. Referring to both of these Figures, the body member 110, priming handle 120, and adjustable stop 140 are shown. In the configuration of FIGS. 3 and 4, the trigger 130 is displaced distally as compared to the primed configuration on FIGS. 1 and 2. As further explained below, the biopsy device 100 may be configured such that displacement of the trigger 130 releases the actuation mechanism of the biopsy device 100, thus displacing cutting elements that may be coupled to the biopsy device 100.

For example, in the embodiment of FIGS. 3 and 4, the trigger 130 may interact with the proximal catches 182 and distal catches 184 of the retention tube 180 such that distal displacement of the trigger 130 with respect to the retention tube 180 causes the proximal catches 182 and distal catches 184 to move out of contact with the traveler flange 152 and impact member flange 162, respectively. Once the proximal catches 182 move out of contact with the traveler flange 152, the spring 190 may displace the traveler 150 in a distal direction. FIG. 4 illustrates the components of the biopsy device 100 at the instant the proximal catches 182 have moved out of contact with the traveler flange 152 in response to displacement of the trigger 130, but before the traveler 150 is displaced by the spring 190.

As further detailed below, the traveler 150 may then move distally until it impacts the impact member 160, the follower 170, or both. As the distal catches 184 are not in contact with the impact member flange 162 in the actuated configuration, such an impact may cause distal displacement of the impact member 160. Also as detailed below, distal displacement of the impact member 160 may cause distal displacement of the follower 170. Additionally, displacement of the trigger 130 in a distal direction may compress the trigger return spring 132, as shown in FIG. 4.

Figure 5A:
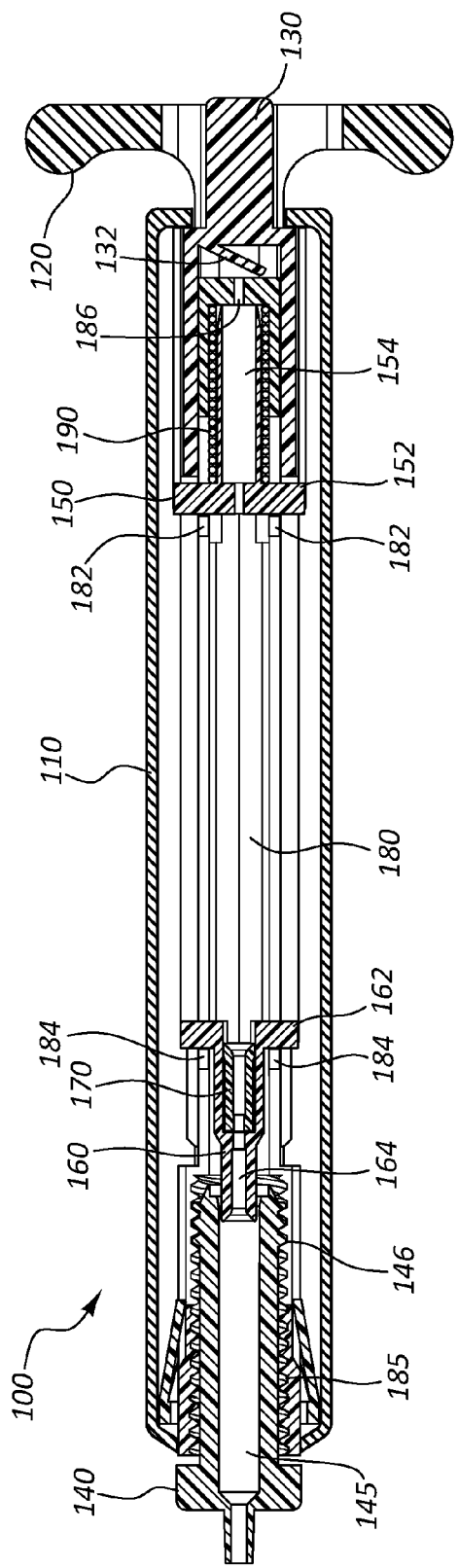
FIG. 5A is a cross-sectional view of the impact biopsy device of FIG. 1 in a first configuration.

FIG. 5A is a cross-sectional view of the impact biopsy device 100 of FIG. 1 in a first configuration. In the configuration of FIG. 5A, the impact biopsy device 100 is in the primed configuration. In this configuration, the spring 190 is loaded, with potential energy stored in the compressed spring 190. Again, in some embodiments other energy sources, such as compressed gas, may be used in connection with, or in place of, a compressed spring 190. In the illustrated embodiment, the proximal catches 182 are engaged with the traveler flange 152 securing the position of the traveler 150 with respect to the retention tube 180. The distal catches 184 are engaged with the impact member flange 162. The trigger 130 is disposed such that distal displacement of the trigger 130 would actuate the biopsy device 100. The priming handle 120 is also shown in this view.

The adjustable stop 140 may comprise threads 146 configured to allow a user to displace the adjustable stop 140 with respect to the retention tube 180 of the biopsy device 100. In the illustrated embodiment the adjustable stop threads 146 are engaged with threads 185 on the retention tube 180. Thus, rotation of the adjustable stop 140 with respect to the retention tube 180 may proximally or distally displace adjustable stop 140 with respect to the retention tube 180. Alternatively or additionally, in some embodiments mechanisms or features other than threads may be configured to allow a user to displace the adjustable stop 140 with respect to the retention tube 180. For example, detents, notches, cams, and so forth may be used.

Figure 5B:
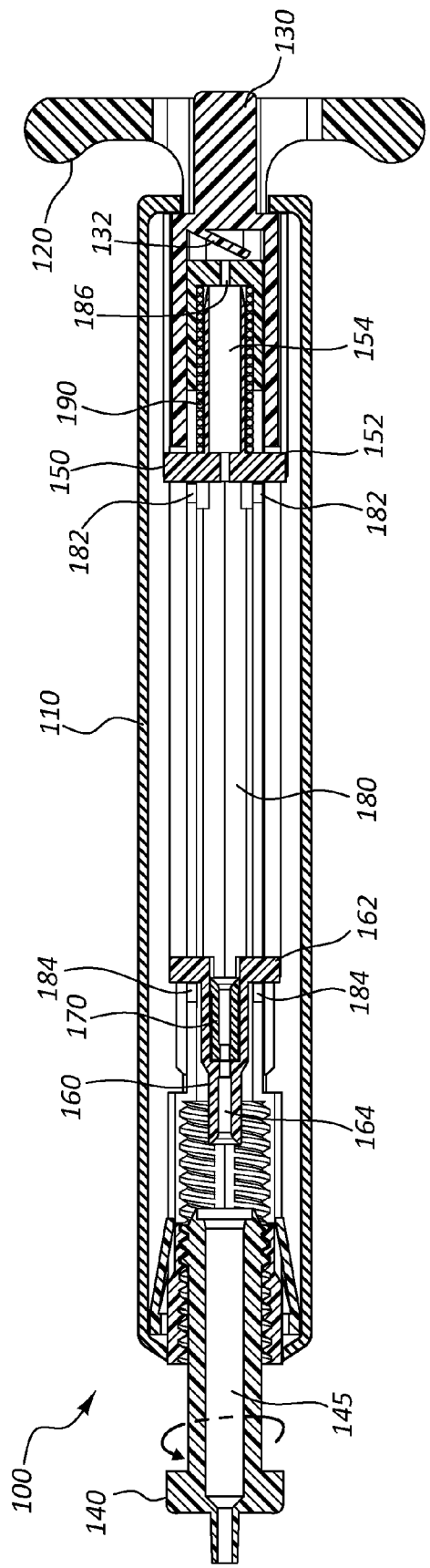
FIG. 5B is a cross-sectional view of the impact biopsy device of FIG. 1 in a second configuration.

For example, FIG. 5B is a cross-sectional view of the impact biopsy device 100 of FIG. 1 in a second configuration. In the configuration of FIG. 5B, the biopsy device 100 is in the primed configuration, as in FIG. 5A. In FIG. 5B, however, the adjustable stop 140 has been distally displaced as compared to the configuration of FIG. 5A.

In some embodiments, displacement of the adjustable stop 140 may be configured to control the length of tissue sample severed by the biopsy device 100. For example, movement of impact member 160 and follower 170 may be controlled by the position of the adjustable stop 140. In some embodiments, as further detailed below, the impact member 160 and follower 170 may be displaced distally due to impact with the traveler 150 until one or both of the impact member 160 and follower 170 contact the adjustable stop 140. In the primed configuration, the position of the impact member 160 and follower 170 may be determined by the distal catches 184 coupled to the retention tube 180, as shown in FIGS. 5A and 5B. Thus, the length of travel of the impact member 160 and follower 170 (and the cutting members coupled thereto) may be adjusted by displacement of the adjustable stop 140 with respect to the retention tube 180.

Interaction of the adjustable stop threads 146 and the retention tube threads 185 may be configured to make the adjustable stop 140 adjustable along a continuous range over which the threads 146, 185 are engaged. In other words, the adjustable stop 140 may be configured such that a practitioner can adjust the length of the sample to be severed by the biopsy device 100, at any relative position along the adjustable path of the adjustable stop 140.

An adjustable stop 140 may facilitate use of the biopsy device 100 in particular therapies or procedures. In some embodiments, the adjustable stop 140 may be adjustable over a continuous range, allowing a practitioner to configure the biopsy device 100 to sever a sample of any length within the range. For example, a practitioner may desire to sever a relatively short tissue sample, such as instances where obtaining a deeper sample would cause unwanted trauma to adjacent tissue. Thus, the practitioner may manipulate the position of the adjustable stop 140 in order to obtain a sample of a desired length while avoiding severing tissue adjacent the sample. Embodiments that utilize distinct catches to position the adjustable stop 140 at particular intervals are also within the scope of this disclosure.

The adjustable stop 140 may be adjustable over a continuous range of any length. For example, the adjustable stop 140 may be configured to allow a practitioner to adjust sample length over a continuous range from 2 mm to 35 mm, including from 5 mm to 30 mm, and from 10 mm to 20 mm. Further, the sample length may be adjustable to lengths less than 2 mm or greater than 35 mm.

As with the configuration of FIG. 5A, in the primed configuration of FIG. 5B, the impact member 160 is engaged with the distal catches 184 of the retention tube 180, the follower 170 is engaged with the impact member 160, the spring 190 is loaded, and the traveler 150 is engaged with the proximal catches 182. The trigger 130 is disposed in the ready to actuate position, with the trigger return spring 132 uncompressed. The priming handle 120 is shown in the same relative position as in FIG. 5A.

FIG. 5C is a cross-sectional view of the impact biopsy device 100 of FIG. 1 in a third configuration. In the configuration of FIG. 5C, the biopsy device 100 has been actuated by distal displacement of the trigger 130 as compared to the primed configuration of FIGS. 5A and 5B. The arrow in FIG. 5C indicates the displacement of the trigger 130.

Thus, the biopsy device 100 may be configured such that a practitioner may depress the trigger 130 in a distal direction to actuate the biopsy device 100. Other types of triggers or actuators, such as handles, levers, sliders, and so forth, are likewise within the scope of this disclosure. As further explained below, actuation of the trigger 130 may be configured to release the actuation mechanism of the biopsy device 100 such that cutting members coupled to the device are displaced to sever a tissue sample.

In the embodiment of FIG. 5C, distal displacement of the trigger 130 moves the proximal catches 182 out of engagement with the traveler flange 152 and the distal catches 184 out of engagement with the impact member flange 162. The components of FIG. 5C are illustrated with the catches 182, 184 moved out of engagement, but before the other elements of the actuation mechanism (such that the spring 190, traveler 150, impact member 160, and follower 170) are displaced. Thus, as shown in FIG. 5C, the spring 190 is still compressed; however, the proximal catches 182 are no longer restraining the traveler 150. In the illustrated configuration, the elements are shown at the instant the spring 190 begins to accelerate and displace the traveler 150.

The adjustable stop 140 is shown in the same position relative to the retention tube 180 as in FIG. 5B. Also, the priming handle 120 is shown in the same relative position as that shown in FIGS. 5A and 5B.

FIG. 5D is a cross-sectional view of the impact biopsy device 100 of FIG. 1 in a fourth configuration. By comparison with FIG. 5C, in the configuration of FIG. 5D, the spring 190 has displaced the traveler 150 in the distal direction. Once the proximal catches 182 no longer restrain the traveler 150, the spring 190 may exert a force separating the traveler 150 from the loading surface 186 of the retention tube 180. This force may displace the traveler 150 in the distal direction, in some instances converting at least a portion of the potential energy stored in the spring 190 to kinetic energy associated with the traveler 150. The traveler 150 may move distally until it impacts the impact member 160. In the illustrated configuration, the traveler 150 is shown at the moment it impacts the impact member 160, before the impact member 160 is displaced due to the contact. In this configuration, because the trigger 130 is depressed distally, the distal catches 184 are moved out of engagement with the impact member 160, allowing the impact member 160 to be displaced due to contact with the traveler 150.

In the configuration of FIG. 5D, the trigger 130 is depressed distally and the trigger return spring 132 compressed. As further discussed below, the trigger return spring 132 may be configured to return the trigger 130 proximally after a user actuates the biopsy device 100. However, because the displacement of the actuation elements as depicted in FIGS. 5B-5E may be completed very quickly, the trigger 130 is still shown as depressed distally in the views of FIGS. 5B-5D. In some embodiments, for example, the displacement of the actuation mechanism components may be complete before a practitioner removes his or her finger from the trigger 130 once the trigger 130 is actuated.

In the illustrated embodiment of FIG. 5D, the spring 190 is shown as expanding such that it remains in contact with the traveler 150 when the traveler 150 impacts the impact member 160. In other embodiments, the spring 190 may be shorter, such that the spring 190 does not maintain contact with the traveler 150 along the entire displacement of the traveler 150 between the primed position and the impact position.

Impact between the traveler 150 and the impact member 160 may accelerate the impact member 160, displacing it in a distal direction. In some embodiments, the traveler flange 152 may be configured to contact the impact member flange 162 when the traveler 150 impacts the impact member 160. FIG. 5E is a cross-sectional view of the impact biopsy device 100 of FIG. 1 in a fifth configuration, with the impact member 160 and follower 170 displaced distally as compared to the configuration of FIG. 5D.

As illustrated in the configuration of FIG. 5E, the traveler 150 may impact the impact member 160 and transfer all, or a substantial portion, of the kinetic energy associated with the traveler 150 to the impact member 160. Thus, after impact, the traveler 150 may remain in essentially the same relative position as that at which impact was made. In some embodiments, the traveler 150 may additionally or alternatively move slightly distally or proximally after impact, may stay in contact with the impact member 160 as the impact member 160 is displaced, or may continue to move distally though at a different rate than the impact member 160. In other embodiments, the traveler 150 may first impact the follower 170 and the impact member 160 may accelerate due to interaction with the follower 170. Still further, in some embodiments, the traveler 150 may be configured to impact both the impact member 160 and the follower 170.

In the embodiment of FIG. 5E, the impact member 160 may be displaced distally after impact, moving until it contacts the adjustable stop 140. Contact with the adjustable stop 140 may be configured to stop the movement of the impact member 160 and, as further detailed below, stop the tissue severing of a cutting member associated with the impact member 160. The follower 170 may be configured to initially be displaced with the impact member 160. In some instances, the follower 170 may be decoupled from the impact member 160 before the impact member 160 reaches the adjustable stop 140, which may cause the follower 170 to stop at a different position or at a different time than the impact member 160. As further outlined below, in some embodiments interaction between the follower 170 and the adjustable stop 140 may stop the displacement of the follower 170 at a position proximal to a position at which the adjustable stop 140 stops the impact member 160. In the configuration of FIG. 5E, the impact member 160 has moved to the end of its travel path distally, such that the impact member 160 is in contact with the adjustable stop 140. The follower 170 is shown in a relatively more proximal position with respect to the impact member 160 as compared to the position of the follower 170 with respect to the impact member 160 in the configuration of FIG. 5D (though both elements have been moved distally with respect to the retention tube 180 between the configurations of FIG. 5D and FIG. 5E). As further detailed below, this offset between the travel distance of the impact member 160 and the follower 170 may be configured to displace cutting members associated with each component such that the cutting members fully sever a tissue sample from the patient.

In the configuration of FIG. 5E, the trigger return spring 132 is shown in an expanded configuration, with the trigger 130 returned proximally to the same position as when the trigger 130 is in the primed configuration. The trigger return spring 132 may be configured to return the trigger 130 to this position after a practitioner actuates the biopsy device 100. Again, the displacement of components within the biopsy device 100 may be configured to take place sufficiently rapidly that the biopsy device 100 is fully actuated before a practitioner removes his or her finger from the trigger 130 after initially activating the biopsy device 100.

With the trigger 130 in a relatively proximal position in the configuration of FIG. 5E, the proximal catches 182 and distal catches 184 may return to a position within the travel paths of the traveler 150 and impact member 160, respectively. However, because the traveler 150 and impact member 160 have been distally displaced, the catches 182, 184 are not engaged with the traveler 150 and impact member 160 in this configuration. The priming handle 120 is also shown in the view of FIG. 5E. Priming catches 122 are also indicated.

FIG. 5F is a cross-sectional view of the impact biopsy device 100 in a sixth configuration, showing the actuation mechanism partially returned to a primed configuration. The biopsy device 100 may comprise a priming handle 120 configured to return the actuation mechanism to a primed configuration.

As shown in FIG. 5F, proximal displacement of the priming handle 120 with respect to the retention tube 180 may proximally displace the priming catches 122. The priming catches 122 may then interact with the impact member flange 162, drawing the impact member 160 proximally as the priming handle 120 is moved proximally. The impact member 160 may reengage the follower 170 as the impact member 160 is moved proximally, moving the follower 170 proximally. Once the impact member 160 reaches its primed position, the distal catches 184 may engage the impact member flange 162 and the priming catches 122 may disengage from the impact member flange 162. In the configuration of FIG. 5F, the impact member 160 and follower 170 are shown returned to the primed position.

The priming catches 122 may then engage the traveler flange 152, proximally displacing the traveler 150 such that the spring 190 is compressed and the traveler 150 returns to engagement with the proximal catches 182. Once the biopsy device 100 is fully primed, the priming handle 120 may be returned distally to the position shown in FIG. 5A. In some embodiments, displacement of the priming handle 120 may be configured to also return the trigger 130 to a prime position, including embodiments that comprise no trigger return spring 132. Further, embodiments wherein the priming handle 120 and trigger 130 are fixedly coupled, comprising a single element configured to both actuate and prime the biopsy device 100, are within the scope of this disclosure.

In some devices, a cutting member may not actually sever tissue unless the cutting member is moving at a sufficient speed or has a sufficient force acting thereon. Thus, placing a cutting member in contact with tissue to be biopsied, then directly accelerating the cutting member through contact with a spring, may crush or deform a proximal end of the tissue sample as the cutting member is accelerated to cutting speed.

In other words, a device that utilizes direct acceleration of a cutting member by a spring may displace the cutting member an amount before the cutting member reaches cutting speed. The proximal end of the tissue sample may be deformed or crushed during this acceleration. Further, such devices may utilize springs with very high spring constants in order to accelerate the cutting member as quickly (and over as short a distance) as possible. Such springs may make an associated device difficult to prime or use, and may create vibrations, noises, or other issues when the device is actuated.

An impact biopsy device, such as impact biopsy device 100 of FIGS. 5A-5F, may be configured to quickly transfer force to a cutting member, and thus may be configured to limit deformation of the tissue sample during cutting. The biopsy device 100 may first accelerate the traveler 150, allowing the traveler to reach a particular speed before any cutting members are displaced. The spring 190 may be configured to accelerate the traveler 150 to an impact speed over a distance (such as the distance the traveler is displaced prior to impact) that may allow use of a spring having a relatively small spring constant, as the traveler is not required to reach impact speed prior to impact with the impact member 160. The "impact speed" of the traveler 150 may be defined as the speed at which the traveler 150 travels in order to impart an impact force sufficient to accelerate the impact member 160 to cutting speed.

Additionally, an impact biopsy device may facilitate severing tissue samples of a variety of lengths. The impact configuration may accelerate cutting members associated with the device to cutting speed without substantially displacing the cutting members. Again, the impact biopsy device may accelerate the traveler 150 over a distance, but the transferred force to the impact member 160 (then to any related cutting members) may not involve acceleration of these members over a distance. Thus, an impact biopsy device may be configured to sever particularly short samples, as the cutting members reach cutting speed without substantial displacement. By comparison, direct acceleration of a cutting member by a spring may require some displacement of the cutting member before the cutting member reaches cutting speed. Thus, the minimum sample length may be at least as long as the displacement needed to bring such a cutting member to cutting speed. Further, an impact biopsy device may be configured such that the cutting members maintain a substantially uniform cutting speed during the severing of an entire sample, rather than accelerating during the first portion of the severing. Samples severed by uniform cutting speeds may be generally more uniform than samples severed by accelerating cutting members, which may deform a portion of the sample.

The potential energy stored in the spring 190 may be expressed by the equation $E=(0.5)kx^2$, where k is the spring constant and x the displacement of the spring 190 in the compressed state. The energy associated with the traveler 150 after it is accelerated by the spring 190 may be expressed as $E=(0.5)mV^2$ where m is the mass of the traveler 150 and V is the velocity of the traveler 150. The exponential factor associated with the potential energy of the spring 190 may also facilitate use of springs with relatively small spring constants in the impact biopsy device 100 of FIGS. 5A-5F.

Accelerating the impact member 160 and follower 170 through an impact force supplied by an already moving traveler 150 may quickly accelerate the impact member 160 and follower 170 (and the associated cutting members), allowing the cutting members to begin severing tissue without initially deforming the tissue.

Furthermore the device may be configured such that no cutting member is directly coupled to the traveler 150. Thus, the biopsy device 100 may be configured such that the spring 190, or any other biasing or energy storage element or system, does not directly exert force on any component coupled directly to a cutting member. Rather, the spring 190, or any other biasing or energy storage element or system, may exert a force to accelerate an intermediate component, such as the traveler 150, which in turn exerts a force on components directly coupled to cutting members, such as the impact member 160 and/or follower 170.

Referencing FIGS. 5A-5F, a practitioner may utilize the impact biopsy device 100 in a variety of procedures. The practitioner may adjust the adjustable stop 140 to any desired point along the continuously adjustable displacement of the adjustable stop 140 to control the length of tissue sample obtained. The practitioner may then advance the device within a patient such that cutting members associated with the biopsy device 100 are adjacent tissue to be biopsied. In some instances, a practitioner may adjust the adjustable stop 140 after first advancing the cutting members.

The practitioner may then actuate the biopsy device 100 by distally displacing the trigger 130. Displacement of the trigger 130 may then release the traveler 150 such that the traveler is accelerated by the spring 190. The traveler 150 may then impact the impact member 160 and follower 170 such that cutting members associated therewith are likewise accelerated. The cutting members may sever a tissue sample, allowing the device to be withdrawn from the patient and the sample obtained.

Figure 6:
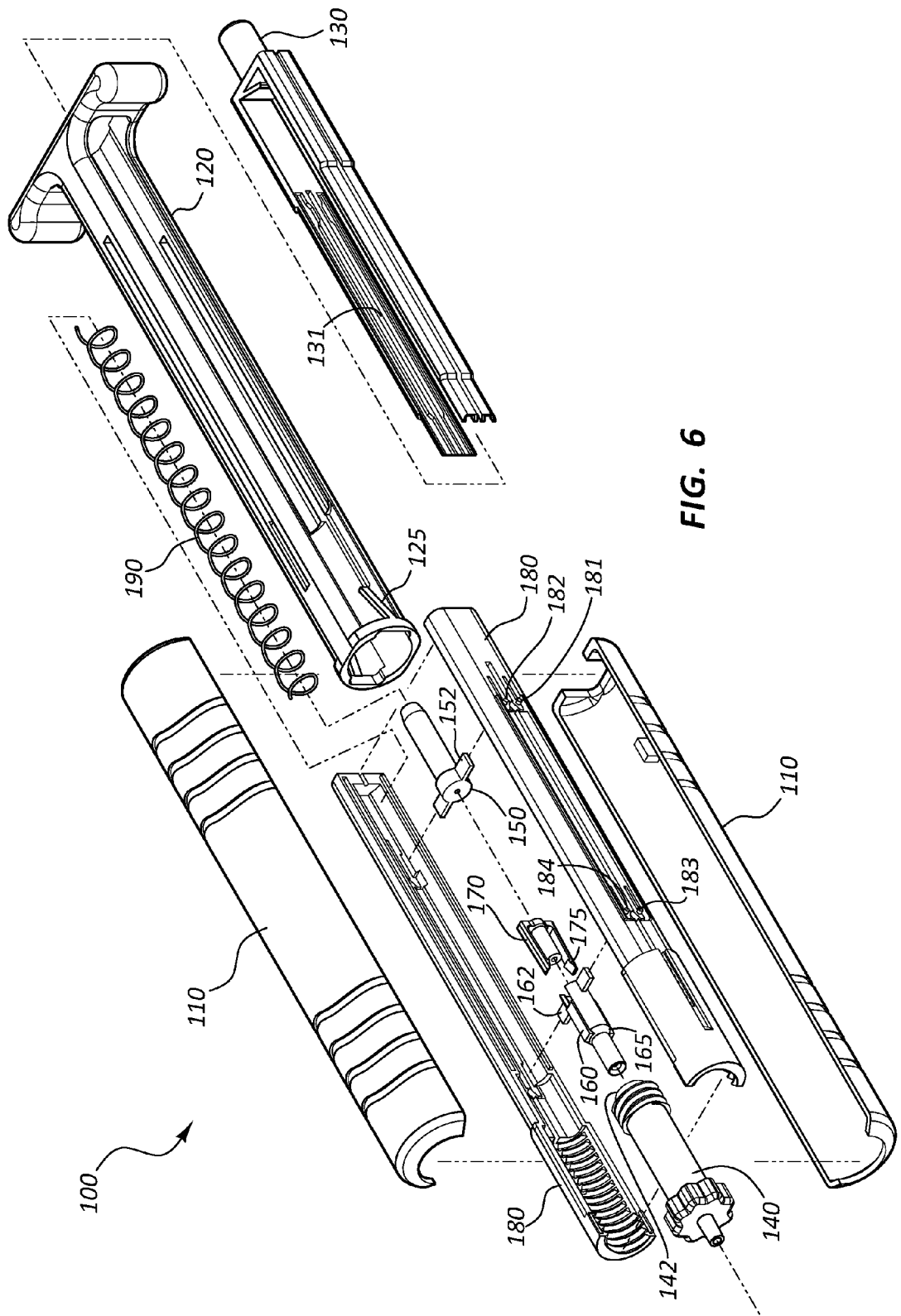
FIG. 6 is an exploded view of the impact biopsy device of FIG. 1.

FIG. 6 is an exploded view of the impact biopsy device 100 of FIG. 1. Below, certain features of the biopsy device 100 and its components are further discussed in connection with this exploded view. The exploded view illustrates the body member 110, the retaining tube 180, and the trigger 130 of the biopsy device 100. The trigger 130 may comprise grooves or ridges 131 configured to interact with protrusions 181, 183 on the proximal 182 and distal 184 catches. Distal displacement of the trigger 130 may cause the ridges 131 to interact with the protrusions 181, 183 such that the proximal 182 and distal 184 catches are pushed apart, thereby separating opposing catches and moving the catches out of engagement with the traveler flange 152 and impact member flange 162.

The follower 170 may comprise follower catches 175 configured to couple the follower 170 to the impact member 160. In some embodiments, the follower catches 175 may be disposed over the impact member 160 such that the follower catches 175 engage impact member protrusions 165. This interaction may cause the follower 170 to be displaced distally when the impact member 160 is so displaced. Further, the adjustable stop 140 may comprise a chamfer 142 configured to interact with the follower catches 175. The follower catches 175 may contact the chamfer 142 such that the follower catches 175 are spread apart and the follower 170 disengages from the impact member 160. In some embodiments, this interaction may also stop the displacement of the follower 170. In some instances the impact member 160 may travel distally beyond the point of disengagement with the follower 170 after the follower catches 175 contact the chamfer 142. Thus, in some instances the impact member 160 may be displaced beyond the follower 170 when the biopsy device 100 is actuated.

Relative positions of the traveler 150 and spring 190 are also shown in the illustrated embodiment. Additionally, the primer handle 120 and primer catches 125 are illustrated.

Figure 7:
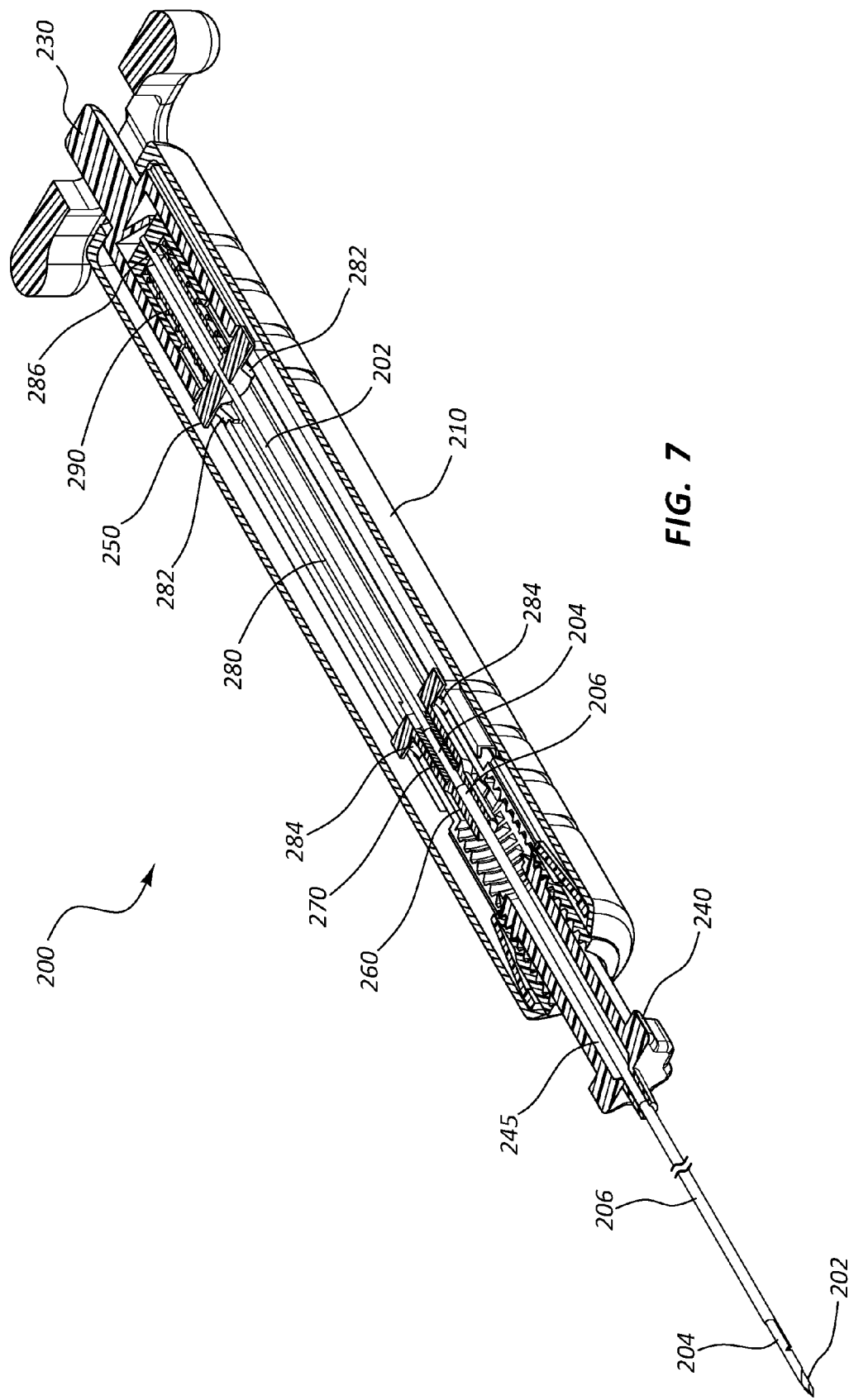
FIG. 7 is a cross-sectional view of another embodiment of an impact biopsy device.

FIG. 7 is a cross-sectional view of another embodiment of an impact biopsy device 200. The embodiment of FIG. 7 may include components that resemble components of the embodiment of FIGS. 1-6 in some respects. For example, the embodiment of FIG. 7 comprises a body member 210 that may be analogous to the body member 110 of the embodiment of FIGS. 1-6. It will be appreciated that all the illustrated embodiments have analogous features and components. Accordingly, like or analogous features are designated with like reference numerals, with the leading digits incremented to "2." Relevant disclosure set forth above regarding similarly identified features thus may not be repeated hereafter. Moreover, specific features of the device and related components shown in FIG. 7 may not be shown or identified by a reference numeral in the drawings or specifically discussed in the written description that follows. However, such features may clearly be the same, or substantially the same, as features depicted in other embodiments and/or described with respect to such embodiments. Accordingly, the relevant descriptions of such features apply equally to the features of the device and related components of FIG. 7. Any suitable combination of the features, and variations of the same, described with respect to the device and components illustrated in FIG. 1 can be employed with the device and components of FIG. 7, and vice versa. This pattern of disclosure applies equally to further embodiments depicted in subsequent figures and described hereafter.

The impact biopsy device 200 of FIG. 7 comprises cutting members (202, 204, 206) coupled to the actuation mechanism. Specifically, the biopsy device 200 comprises a stylet 202 that extends along a central axis of the biopsy device 200 and is coupled to a retention tube 280 adjacent a loading surface 286 of the retention tube 280. As the biopsy device 200 may be configured to operate analogously to the biopsy device 100 described in connection with FIGS. 1-6, various components of the actuation mechanism may be configured to accommodate the stylet 202, while still configured to displace as described in connection with the embodiment of FIGS. 1-6. For example, the stylet 202 may be disposed such that openings or central lumens of a traveler 250, impact member 260, follower 270, and adjustable stop 240 allow these components to move along the length of the stylet 202. In the illustrated embodiment, the stylet 202 extends from the loading surface 286 of the retention tube 280 through the adjustable stop lumen 245 to the outside of the body member 210.

The biopsy device 200 may be configured such that the retention tube 280 does not move with respect to the body member 210 when the device is actuated. Further, the stylet 202 may be fixedly coupled to the retention tube 280. Thus, in some instances a practitioner may grasp the body member 210, using it as a handle, to advance the stylet 202 to a position within a patient's body as part of a procedure.

In the illustrated embodiment, the biopsy device 200 further comprises a cannula 204 coupled to the follower 270 and an outer tubular member 206 coupled to the impact member 260. When the biopsy device 200 is actuated by displacement of a trigger 230, proximal catches 282 may release the traveler 250, allowing it to accelerate and impact the impact member 260. Analogous to the actuation described in connection with the previous embodiment, the impact member 260 and follower 270 may then displace distally, which, in turn, displaces the outer tubular member 206 and cannula 204 distally. As described in connection with the embodiment of FIGS. 1-6, a biopsy device may be configured such that the impact member 260 travels a longer distance than the follower 270 when the device is actuated. Accordingly, in some embodiments the cutting member coupled to the impact member 260 (the outer tubular member 206 in the embodiment of FIG. 7) may be displaced over a longer distance than the cutting member coupled to the follower 270 (the cannula 204 in the embodiment of FIG. 7). Elements of the actuation assembly coupled to cutting members of the embodiment of FIG. 7 are further discussed in connection with FIGS. 8A-8E, below.

FIGS. 8A-8E are side views of a portion of the impact biopsy device 200 of FIG. 7 in five different configurations. FIGS. 8A-8E illustrate an example of how the cutting members may be displaced when the biopsy device is actuated. The disclosure below, referencing FIGS. 8A-8E, may also reference elements of the biopsy device 200 shown in FIG. 7, but not shown in the views of FIGS. 8A-8E.

In the configuration of FIG. 8A, the stylet 202 extends from the cannula 204 and the outer tubular member 206 is disposed around the cannula 204. A cutting element 207 coupled to the outer tubular member 206 is shown disposed proximally of a notch 205 in the cannula 204. These members may be disposed as shown in FIG. 8A when the biopsy device 200 is in a primed configuration. In this configuration, a practitioner may advance the cutting members to a position within the body adjacent tissue to be biopsied. The stylet 202 may be configured with a sharp distal end to facilitate advancement of the cutting members through body tissue, including percutaneous access.

In the configuration of FIG. 8B, the cannula 204 and outer tubular member 206 are being displaced distally with respect to the stylet 202. As described above, upon actuation, the traveler 250 may impact the impact member 260, causing the impact member 260 to be displaced distally. The follower 270 may be coupled to the impact member 260 along a portion of this displacement. Thus, the outer tubular member 206, coupled to the impact member 260, and the cannula 204, coupled to the follower 270, may be simultaneous displaced when the biopsy device 200 is actuated. As long as the follower 270 is coupled to the impact member 260, the position of the cannula 204 with respect to the outer tubular member 206 may not change.

FIG. 8C illustrates the cutting members after the follower 270 is disengaged from the impact member 260. As described above (including in connection with the embodiment of FIGS. 1-6), the biopsy impact device 200 may be configured such that the impact member 260 is displaced over a longer distance than the follower 270 when the biopsy device 200 is actuated. Once the follower 270 is disengaged from the impact member 260, the outer tubular member 206 may be distally advanced with respect to the cannula 204. This displacement may cause the cutting element 207 to interact with the notch 205 such that the cutting element 207 passes through the notch 205 into the interior of the cannula 204.

FIGS. 8B and 8C illustrate how the cutting members may sever a tissue sample from the body. As the cannula 204 is advanced with respect to the stylet 202, a distal end of the cannula 204 may sever the longitudinal length of a tissue sample. Advancement of the outer tubular member 206 with respect to the cannula 204 may then cause the cutting element 207 to sever the distal end of the tissue sample. The tissue sample may then be disposed within the cannula 204 between the cutting member 207 and the distal end of the stylet 202, in the configuration shown in FIG. 8C. As described above, adjustment of the adjustable stop 240 may control the length of travel of the impact member 260 and follower 270. Thus, the adjustable stop 240 may be configured to control the length of the tissue sample severed by the biopsy device 200.

As shown in FIG. 8D the entire assembly may then be removed from the patient, along with the tissue sample still disposed within the cannula 204. FIG. 8E illustrates the cutting members as the impact biopsy device 200 is primed. Priming draws the cannula 204 and outer tubular member 206 proximally with respect to the stylet 202, removing the cutting element 207 from the notch 205 and forcing the tissue sample out of the cannula 204, due to interaction with the stylet 202.

Various cutting elements may be configured to use in connection with an impact biopsy device as disclosed herein. Depending on the desired relative displacement of the cutting members, each member may be coupled to a particular element of an impact biopsy device actuation mechanism. Further, elements of the mechanism may be configured to allow for desired offsets or relative displacements of cutting members. For example, in the embodiment of FIGS. 9A-9C, the cutting members may be configured with a larger difference in total displacement than the difference between the total displacement of the cannula 204 and outer tubular member 206 of FIGS. 8A-8E.

Figure 9A:
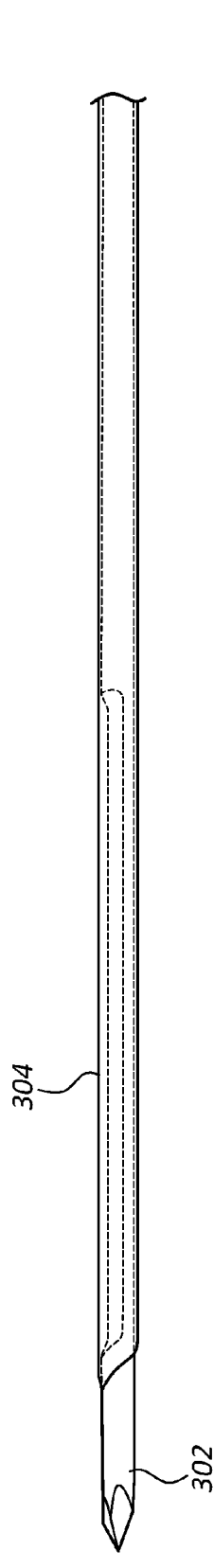
FIG. 9A is a side view of another embodiment of a portion of an impact biopsy device in a first configuration.
Figure 9B:
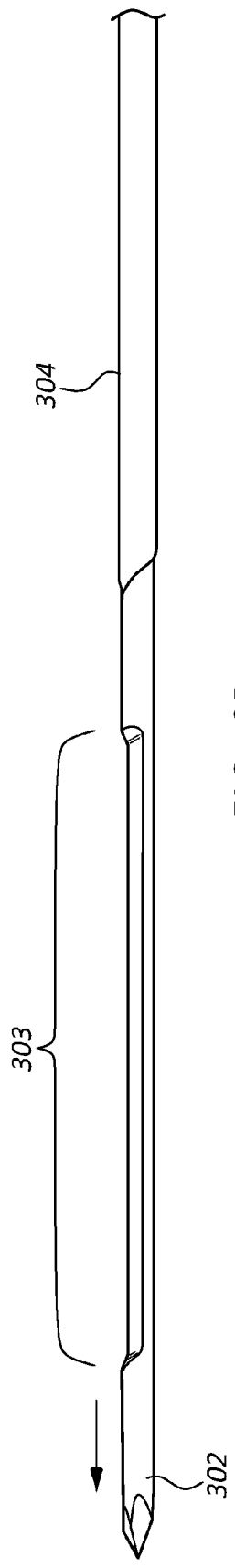
FIG. 9B is a side view of a portion of the impact biopsy device of FIG. 9A in a second configuration.
Figure 9C:
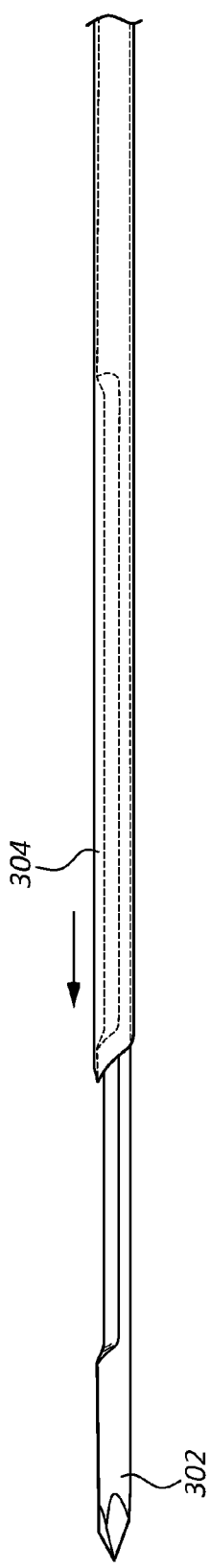
FIG. 9C is a side view of a portion of the impact biopsy device of FIG. 9A in a third configuration.

FIGS. 9A-9C are side views of another embodiment of a portion of an impact biopsy device. These figures illustrate a stylet 302 and a cannula 304. The cutting members may be advanced to a position within the body adjacent tissue to be biopsied in the configuration shown in FIG. 9A. Upon actuation of the device, the stylet 302 may extend from the cannula 304, exposing a trough 303 in the stylet 302, as shown in FIG. 9B. Tissue may then prolapse into the trough 303, filling the void of the trough 303. Advancement of the cannula 304 may sever the length and end of the tissue within the trough 303, severing a tissue sample from the body. The cannula 304 and stylet 302 may then be withdrawn to retrieve the tissue sample. The cannula 304 and stylet 302 may be coupled to elements of an impact biopsy device configured to displace the cannula 304 and stylet 302 as shown.

FIGS. 10-13 illustrate another embodiment of an impact biopsy device 400 in a primed configuration. This biopsy device 400 is analogous to the other biopsy devices disclosed herein. For example, and as further outlined below, the biopsy device 400 comprises a traveler 450, impact member 460, and follower 470. While these components function in an analogous manner to similarly named components of other embodiments disclosed herein, certain distinctions with respect to each member are outlined below in connection with FIGS. 10-13.

Figure 10:
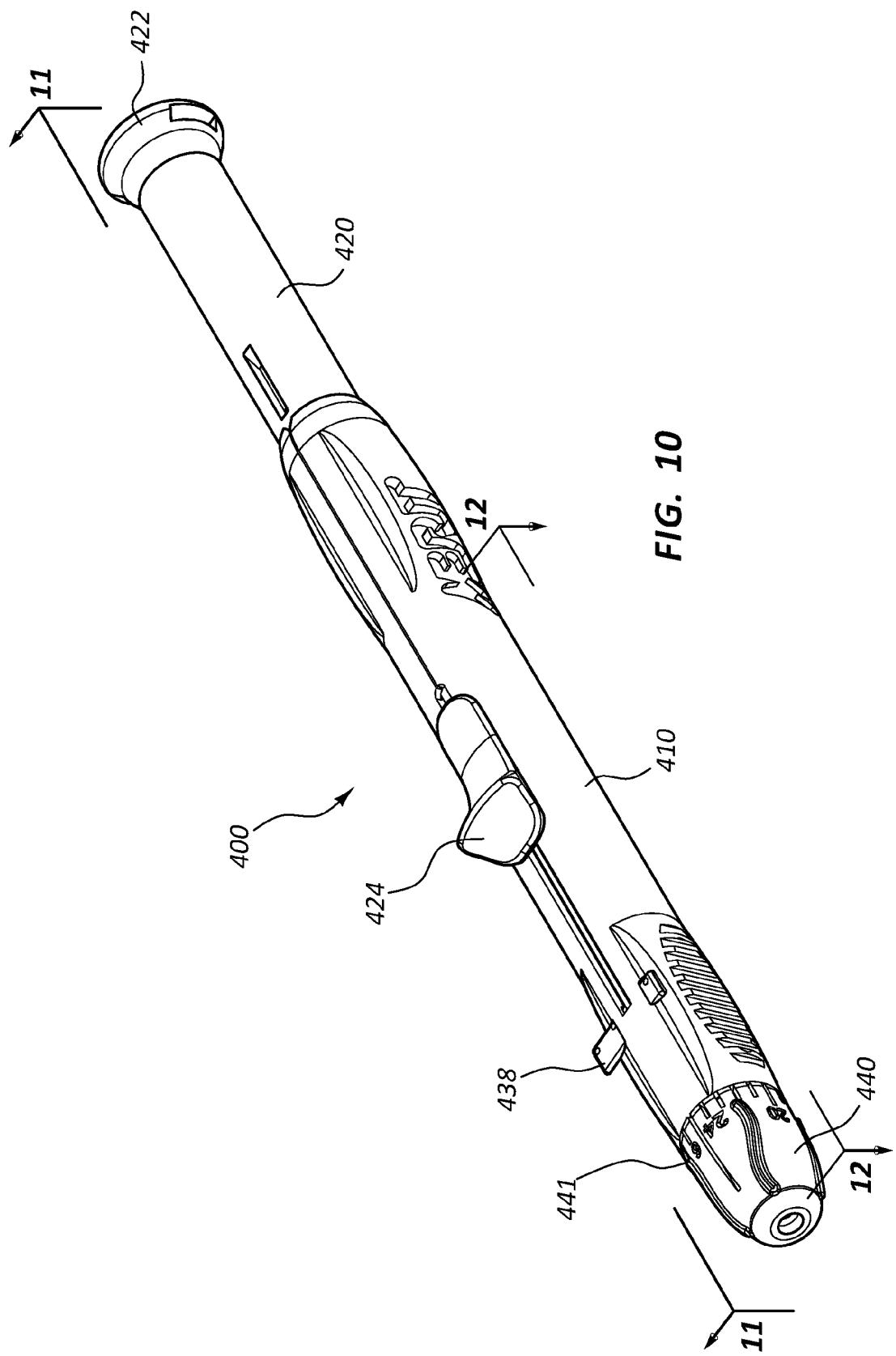
FIG. 10 is a perspective view of another embodiment of an impact biopsy device in a primed configuration.

The biopsy device 400 comprises a body member 410 that may be configured to be grasped by a practitioner when the biopsy device 400 is in use. Thus, in some embodiments, the body member 110 may comprise a handle. The biopsy device 400 further comprises a priming handle 420. In the embodiment of FIG. 10, the priming handle 420 comprises an end input 422 and a longitudinal input 424. As further detailed below either the end input 422 and the longitudinal input 424 may be utilized by a user to prime the biopsy device 400. Proximal displacement of the priming handle 420 is configured to prime the biopsy device 400. In some embodiments, proximal displacement of either the end input 422 or the longitudinal input 424 may proximally displace the priming handle 420.

In the illustrated embodiment, the biopsy device 400 further comprises an adjustable stop 440. Indicia 441 on the adjustable stop may be configured to relate the rotational position of the adjustable stop 440 with the longitudinal displacement of one or more components of the biopsy device 400.

Figure 11:
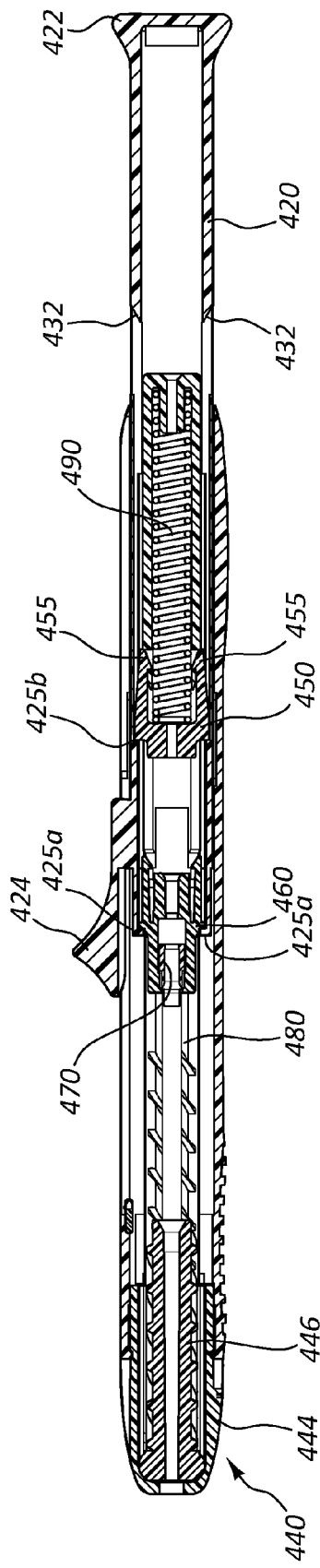
FIG. 11 is a cross-sectional view, taken through plane 11, of the impact biopsy device of FIG. 10.
Figure 12:
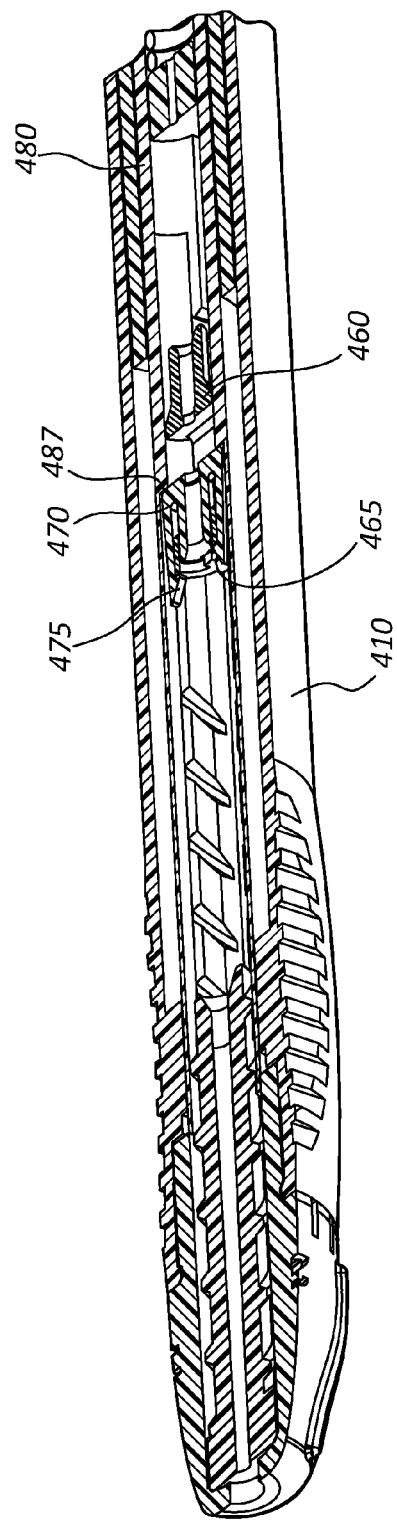
FIG. 12 is a cross-sectional view, taken through plane 12, of the impact biopsy device of FIG. 10.
Figure 13:
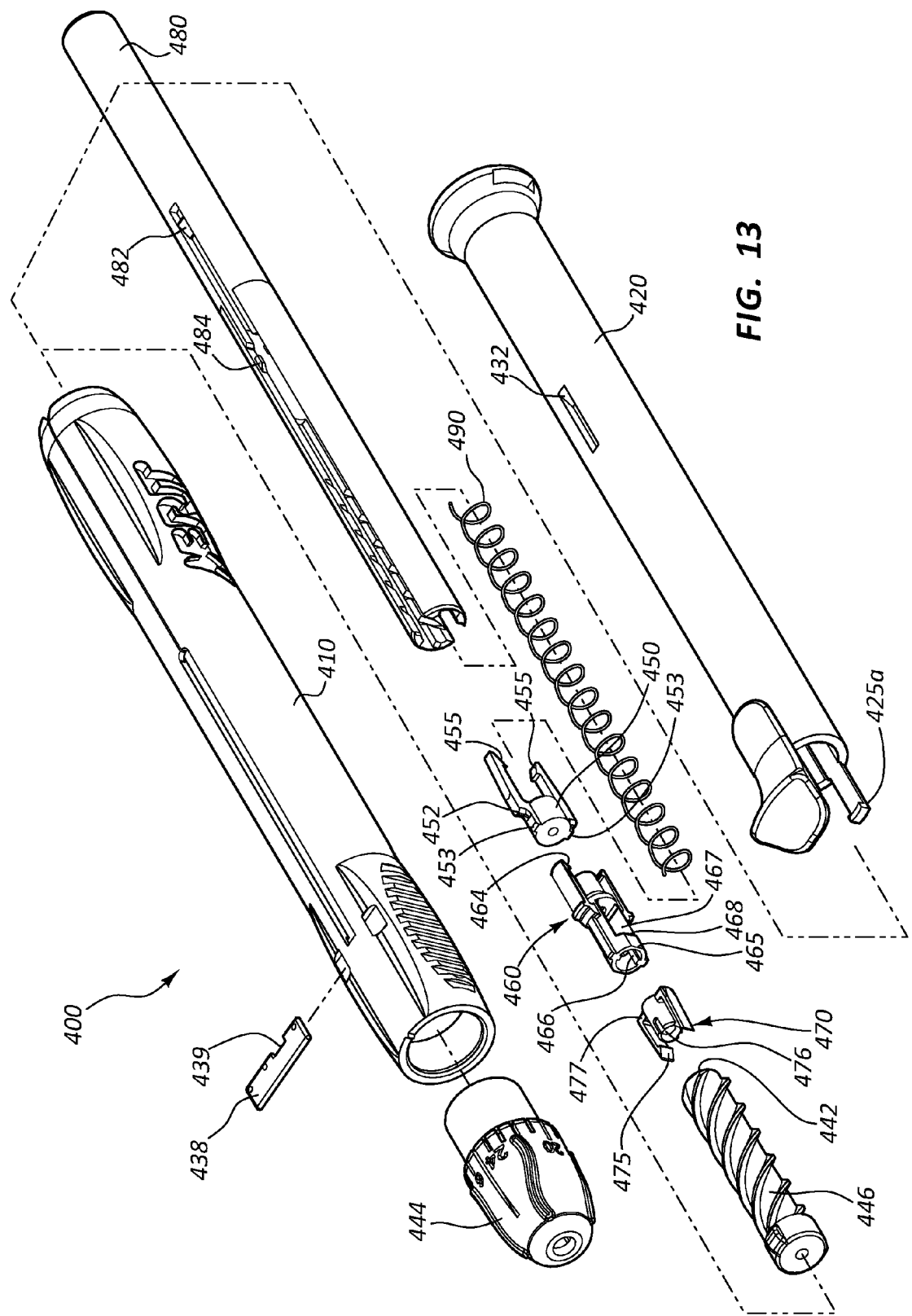
FIG. 13 is an exploded view of the impact biopsy device of FIG. 10.

FIG. 11 is a cross-sectional view, taken through plane 11, of the impact biopsy device 400 of FIG. 10; FIG. 12 is a cross-sectional view, taken through plane 12, of the impact biopsy device 400 of FIG. 10; and FIG. 13 is an exploded view of the impact biopsy device 400 of FIG. 10. Referencing FIGS. 11-13, the biopsy device 400 may comprise a traveler 450, an impact member 460, and a follower 470. As with other embodiments described herein, displacement of the traveler 450, impact member 460, and follower 470 may be configured to displace one or more cutting members, for example biopsy needles, during a procedure.

As shown in FIGS. 11 and 13, the biopsy device 400 may comprise a biasing member such as spring 490. When the biopsy device 400 is in a primed configuration, the spring 490 may be at least partially compressed such that potential energy is stored in the spring 490. Further, in the primed configuration the traveler 450, impact member 460, and follower 470 may each be disposed at the proximal-most points of each components' path of travel during operation.

Still referencing FIGS. 11 and 13, in the primed configuration, the traveler 450 is disposed such that traveler catches 455 of the traveler 450 are engaged with proximal catches 482 of a retention tube 480 of the biopsy device 400. Similarly, impact member catches 464 of the impact member 460 are engaged with distal catches 484 of the retention tube 480. The spring 490 is compressed between the traveler 450 and a proximal end of the retention tube 480. In the primed configuration, the traveler 450 is thus longitudinally offset from the impact member 460 such that upon actuation of the device, the traveler 450 moves longitudinally along this offset before contacting the impact member 460.

Referring to FIGS. 11 and 12, in the primed configuration, follower catches 475 of the follower 470 are engaged with a distal edge 465 of the impact member 460. Due to this interaction, when the impact member 460 is initially displaced distally during actuation of the biopsy device 400, the follower 470 is also displaced, maintaining the same position with respect to the impact member 460.

Referring to FIGS. 11-13, priming the biopsy device 400 may comprise proximal displacement of the priming handle 420 with respect to the retention tube 480. Such displacement may be the result of user input at the end input 422, the longitudinal input 424, or both. As the priming handle 420 is proximally displaced, primer catches 425a adjacent a distal end of the priming handle 420 may engage a distal edge 465 of the impact member 460. Thus, proximal displacement of the priming handle 420 may simultaneously proximally displace the impact member 460 when the primer catches 425a and the distal edge 465 are engaged.

After the biopsy device 400 has been actuated, and before it is primed, the follower 470 may be positioned within the impact member 460 such that the follower catches 475 are proximal of an inside edge 468 of the impact member 470. In the exploded view of FIG. 13, the follower 470 is illustrated adjacent the impact member 460. In this arrangement each part can be viewed separately. When assembled, however, the follower 470 is disposed coaxially with, and within, the impact member 460 such that the radial protrusions 477 that extend from the follower 470 and are coupled to the follower catches 475 extend through side openings 467 in the impact member 460. FIGS. 11 and 12 illustrate these components in an assembled state.

Thus, proximal displacement of the impact member 460 may also proximally displace the follower 470 as the inside edge 468 may act on the follower catches 475. Alternatively, as the impact member 460 is proximally displaced, the follower catches 475 may slip past the inside edge 468 such that an inside ridge 466 of the impact member 460 engages a slot 476 of the follower 470. In either scenario, the follower 470 will be proximally displaced with the impact member 460 during priming.

Again referring to FIGS. 11-13, proximal displacement of the priming handle 420 during priming may thus proximally displace the impact member 460 and follower 470 until the impact member catches 464 engage the distal catches 484 of the retention tube 480. If the follower catches 475 did not slip distally past the inside edge 468 of the impact member 460, an annular ridge 487 (shown in FIG. 12) may engage the follower 470, halting its proximal displacement before the impact member 470 is fully at the primed position. This annular ridge 487 thus ensures the follower catches 475 will slip past the inside edge 468 of the impact member 460 and that the follower catches 475 will be engaged with the distal edge 465 of the impact member 470 when the biopsy device 400 is in the primed configuration.

Moreover, as the priming handle 420 is proximally displaced with respect to the retention tube 480 to prime the biopsy device 400, a primer catch 425b engages the traveler 450 to proximally displace the traveler 450 with respect to the retention tube 480. This primer catch 425b may comprise a distal end of one or more inside grooves on the inside diameter of the retention tube 480. In such embodiments the traveler catches 455 may comprise distal traveler catch shoulders 452 that engage primer catch 425b. The traveler 450 may be proximally displaced until the traveler catches 455 engage the proximal catches 482 of the retention tube 480. Proximal displacement of the traveler 450 with respect to the retention tube 480 compresses the spring 490 between the traveler 450 and a proximal end of the retention tube 480.

When the spring 490 is compressed, the traveler catches 455 are engaged with the proximal catches 482 of the retention tube 480, the impact member catches 464 are engaged with the distal catches 484 of the retention tube 480, the follower catches 475 are engaged with the distal edge 465 of the impact member 470, and the biopsy device 400 is primed and ready for use.

In contrast with the biopsy device 100 of FIG. 1 discussed above, the biopsy device 400 of FIGS. 10-13 does not comprise a separate trigger (such as 130 of FIG. 1). Rather, the priming handle 420 of the embodiment of FIGS. 10-13 may be displaced to actuate the biopsy device 400. Specifically, when the biopsy device 400 is in a primed configuration, distal displacement of the priming handle 420 with respect to the retention tube 480 will cause trigger surfaces 432 of the priming handle 420 to displace the traveler catches 455 radially outward. This displacement causes the traveler catches 455 to be out of engagement with the proximal catches 482 of the retention tube 480. Once the traveler catches 455 and proximal catches 482 are disengaged, the spring 490 may expand and force the traveler 450 to be displaced proximally.

The traveler 450 may then strike the impact member 460, transferring kinetic energy to the impact member 460. At the time of impact, disengagement surfaces 453 on the traveler 450 may displace the impact member catches 464 radially outward and out of engagement with the distal catches 484 of the retention tube 480. The impact member 460 will then be displaced distally due to the transfer of kinetic energy.

The follower 470 will be distally displaced with the impact member 460 until the follower catches 475 contact a chamfer 442 on the proximal end of a threaded portion 446 of the adjustable stop 440. The chamfer 442 forces the follower catches 475 radially outward, out of engagement with the distal edge 465 of the impact member 460 and stops the distal displacement of the follower 470. Thus, as in other embodiments, a cutting instrument coupled to the impact member 460 may be configured to travel farther than a cutting instrument coupled to the follower 470.

The biopsy device 400 may further comprise a safety 438 configured to prevent accidental actuation of the biopsy device 400. As shown in FIGS. 10 and 13, the safety 438 of the illustrated embodiment comprises a rectangular member that may be transversely displaceable with respect to the body member 410. The safety 438 may comprise an opening 439. The safety 438 may be configured to prevent distal displacement of the priming handle 420 beyond a safety point due to interference between the safety 438 and a portion of the priming handle 420. The biopsy device 400 may be configured such that only proximal displacement of the priming handle 420 beyond the safety point will trigger the biopsy device 400. When the safety 438 is positioned such that the opening 439 is aligned with the priming handle 420, the priming handle 420 may be displaced distally beyond the safety point, allowing for actuation of the biopsy device 400.

In contrast with the embodiment of FIG. 1, above, the adjustable stop 440 of the biopsy device 400 of FIGS. 10-13 may comprise a cap portion 444 and a threaded portion 446. The cap portion 444 may be coupled to the threaded portion 446 such that rotation of the cap portion 444 causes rotation of the threaded portion 446 while the threaded portion 446 is allowed to displace longitudinally with respect to the cap portion 444. For example, a ridge of the threaded portion 446 may be displaced within a slot of the cap portion 444, such that the ridge and slot may transfer rotational displacement of the cap portion 444 without restraining longitudinal displacement of the threaded portion 446.

Such an arrangement allows the threaded portion 446 to be longitudinally displaceable with respect to the retention tube 480 as the cap portion 444 and threaded portion 446 are rotated (via interaction of mating threads of the threaded portion 446 and retention tube 480, for example) without longitudinal displacement of the cap portion 444. In the illustrated embodiment, indicia 441 on the cap portion 444 correlate with the longitudinal displacement of the threaded portion 446, allowing a practitioner to adjust and/or set the stroke length through rotation of the cap portion 444 and observation of the relative position of the indicia 441, with respect, for example, to the body member 410.

Figure 14:
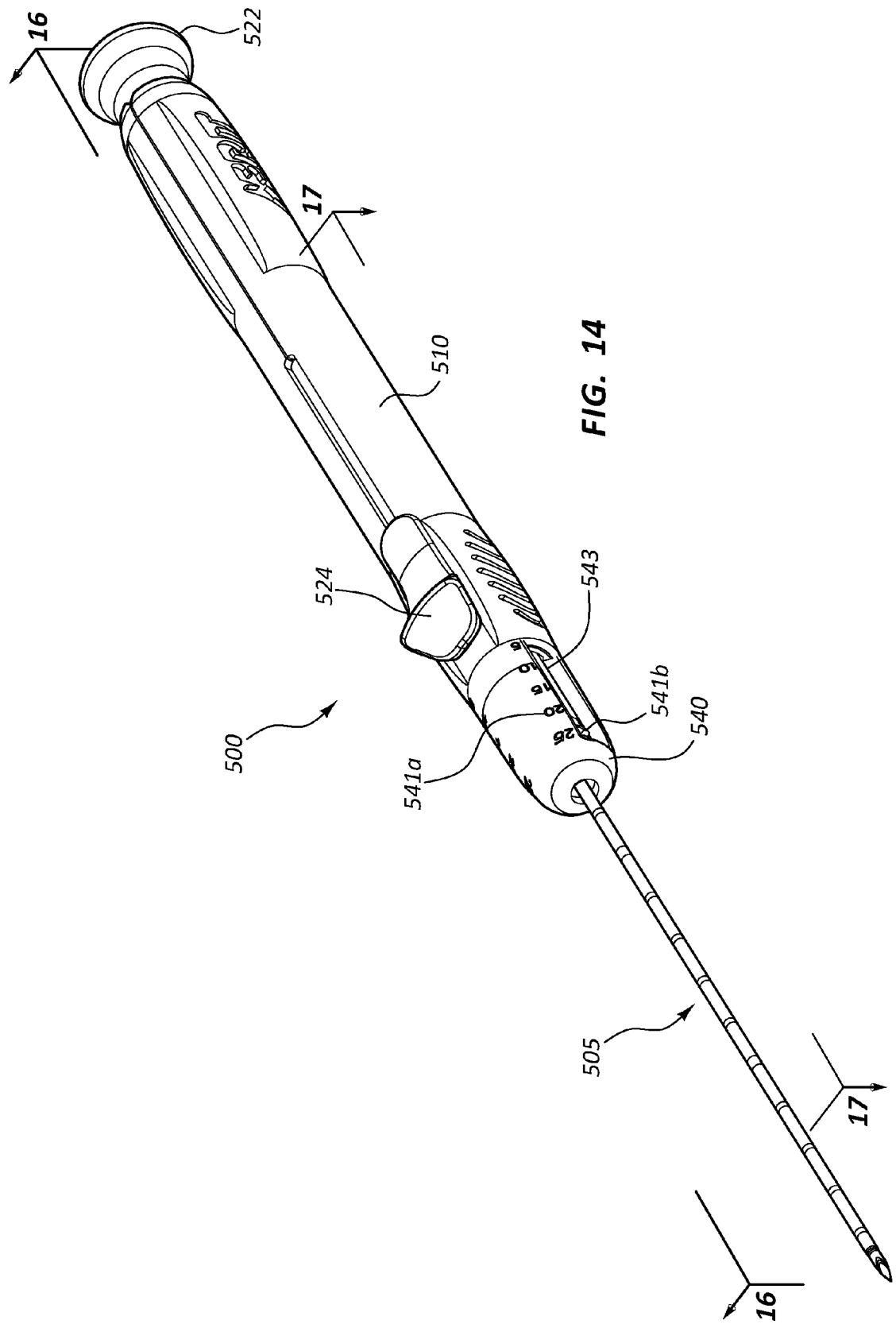
FIG. 14 is a perspective view of another embodiment of an impact biopsy device.
Figure 15:
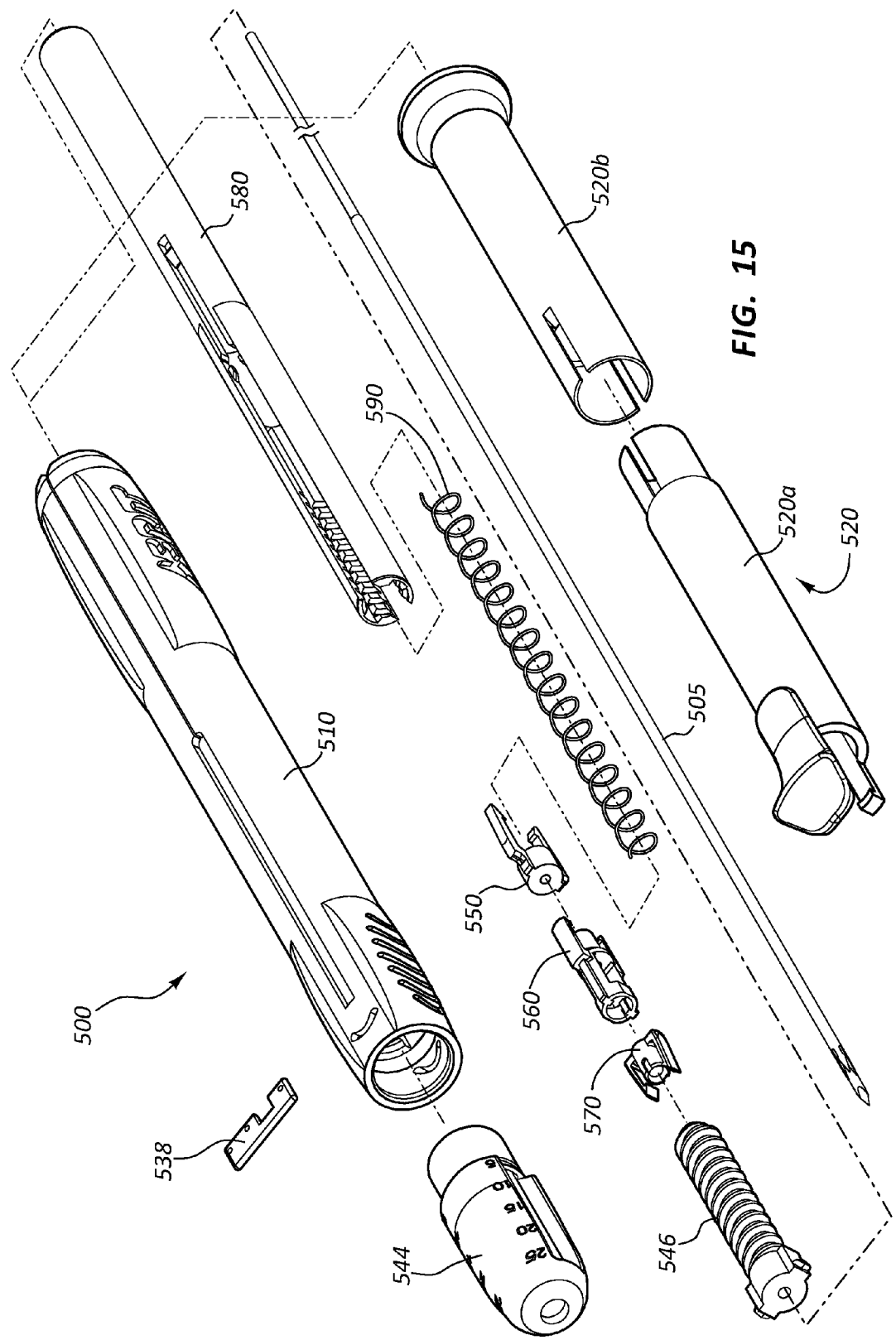
FIG. 15 is an exploded view of the impact biopsy device of FIG. 14.

FIG. 14 is a perspective view of another embodiment of an impact biopsy device 500. FIG. 15 is an exploded view of the impact biopsy device 400 of FIG. 14. The biopsy device 500 is analogous to the biopsy device 400 of FIG. 10, and the other embodiments disclosed herein, in many respects. The biopsy device 500 comprises a body member 510, priming handle 520, safety 538, adjustable stop 540, traveler 550, impact member 560, follower 570, retention tube 580, and spring 590. Each of these elements function in an analogous manner to like elements discussed in connection with the embodiment of FIG. 10. As with the embodiment of FIG. 10, the priming handle 520 comprises an end input 522 and a longitudinal input 524 and the adjustable stop 540 comprises a cap portion 544 and a threaded portion 546.

In contrast to the embodiment of FIG. 10, the priming handle 520 comprises a distal portion 520a and a proximal portion 520b. These portions may be formed separately then coupled during assembly of the biopsy device 500. Also, in contrast to the embodiment of FIG. 10, the cap portion 544 of the adjustable stop 540 comprises an opening 543. The adjustable stop 540 further comprises indicia 541a arranged longitudinally along the cap portion 544 as well as a pointer 541b on the threaded portion 546. Rotation of the cap portion 544, and subsequent longitudinal displacement of the threaded portion 546 with respect to the cap portion 544, will displace the pointer 541b with respect to the indicia 541a. These indicia may correlate with stroke length, allowing a practitioner to set and adjust stroke length by rotation of the cap portion 544 and reference to the indicia 541a and pointer 541b.

With regard to this embodiment, or any embodiment disclosed herein, detents or other features that create a tactile response and/or tend to maintain the rotational position of the adjustable stop 540, once set by a practitioner, are within the scope of this disclosure. A cutting member assembly 505 is coupled to the biopsy device 500 of FIGS. 14 and 15. Again it is within the scope of this disclosure to use any cutting member or assembly in connection with any handle or triggering mechanism disclosed herein.

Without further elaboration, it is believed that one skilled in the art can use the preceding description to utilize the present disclosure to its fullest extent. The examples and embodiments disclosed herein are to be construed as merely illustrative and exemplary and not a limitation of the scope of the present disclosure in any way. It will be apparent to those having skill in the art, and having the benefit of this disclosure, that changes may be made to the details of the above-described embodiments without departing from the underlying principles of the disclosure herein.

The invention claimed is:

1. A tissue biopsy device, comprising:
   a handle configured to be grasped by a user;
   a needle assembly comprising a cannula, the needle assembly operably coupled to the handle, the needle assembly configured to sever a tissue sample; and
   an actuator assembly operably coupled to the handle and needle assembly, the actuator assembly comprising:
      a biasing member;
      a traveling member configured to be displaced by the biasing member when the actuator assembly is actuated;
      a follower; and
      an impact member coupled to the needle assembly, the impact member configured to displace at least a portion of the needle assembly when the traveling member impacts the impact member;
   wherein the cannula is fixedly coupled to the follower, the follower is releasably coupled to the impact member, and the follower is configured to decoupled from the impact member such that the impact member travels a longer distance than the follower when the device is actuated.

2. The biopsy device of claim 1, wherein the traveling member is displaced over a distance before impacting the impact member.

3. The biopsy device of claim 1, wherein the biasing member does not directly exert a force on the impact member when the device is actuated.

4. The biopsy device of claim 1, wherein kinetic energy associated with the traveling member is transferred to the impact member to accelerate the impact member when the device is actuated.

5. The biopsy device of claim 1, wherein the needle assembly further comprises an outer tubular member, and wherein the outer tubular member is fixedly coupled to the impact member and the cannula is releasably coupled to the impact member.

6. The biopsy device of claim 5, further comprising an adjustable stop member operably coupled to the handle, the adjustable stop member configured to stop the movement of the impact member with respect to the adjustable stop member after the traveling member impacts the impact member, and wherein a longitudinal position of the adjustable stop member is adjustable over a continuous range.

7. The biopsy device of claim 6, wherein the adjustable stop member comprises a first portion configured to rotate without longitudinal displacement and a second portion configured to displace longitudinally as the first portion is rotated.

8. The biopsy device of claim 6, wherein contact between the adjustable stop member and the follower decouples the cannula base from the impact member.

9. A tissue biopsy device comprising:
   a handle configured to be graspable by a user;
   a biasing member operably coupled to the handle, the biasing member configured to store potential energy when the biopsy device is in a primed configuration;
   a traveling member operably coupled to the handle, the traveling member disposed such that the potential energy stored in the biasing member is at least partially converted to kinetic energy associated with the traveling member when the biopsy device is actuated;
   an impact member operably coupled to the handle and to the biasing member, the device configured such that the traveling member impacts the impact member when the biopsy device is actuated such that the impact member is displaced relative to the handle and;
   a follower;
   wherein the impact member is coupled to the follower when the biopsy device is in a primed configuration and wherein the follower is initially displaced with the impact member when the device is actuated and
   wherein the follower decouples from the impact member such that the follower travels a shorter longitudinal distance than the impact member when the biopsy device is acutated.

10. The biopsy device of claim 9, wherein the traveling member is disposed adjacent the biasing member when the biopsy device is in a primed configuration and wherein the traveling member is displaced over a first longitudinal distance when the biopsy device is actuated.

11. The biopsy device of claim 10, wherein the traveling member is not in contact with the impact member before displacement over the first longitudinal distance.

12. The biopsy device of claim 11, wherein the biasing member is exerting a biasing force on the traveling member when the traveling member impacts the impact member.

13. The biopsy device of claim 10, wherein the impact member is displaced over a second longitudinal distance after the traveling member impacts the impact member.

14. The biopsy device of claim 13, wherein the second longitudinal distance is adjustable over a continuous range.

15. The biopsy device of claim 13, wherein the follower decouples from the impact member before the impact member is displaced over the entire second longitudinal distance such that the follower travels a shorter longitudinal distance than the second longitudinal distance when the biopsy device is actuated.

16. The biopsy device of claim 15, wherein the impact member is coupled to an outer tubular member comprising a cutting element and the follower is coupled to a cannula.

17. The biopsy device of claim 13, wherein the follower decouples from the impact member such that the follower travels a longer longitudinal distance than the second longitudinal distance when the biopsy device is actuated.

18. A method of obtaining a tissue sample through actuation of a biopsy device, the method comprising:
   releasing a traveling member such that the traveling member is displaced a first longitudinal distance along the biopsy device;
   impacting the traveling member with an impact member such that the impact member is displaced a second longitudinal distance along the biopsy device;

displacing a follower releasably coupled to the impact member and decoupling the follower from the impact member such that the follower travels a shorter distance the second longitudinal distance; and displacing a first cutting member coupled to the impact member such that the cutting member severs a first portion of the tissue sample.

19. The method of claim 18, further comprising storing potential energy in a biasing member prior to releasing the traveling member.

20. The method of claim 18, further comprising storing energy in a chamber of compressed gas prior to releasing the traveling member.

21. The method of claim 18, further comprising displacing a second cutting member, releasably coupled to the impact member, the second cutting member displaced such that the second cutting member severs a second portion of the tissue sample.

22. The method of claim 21, wherein the first cutting member is displaced a distance substantially equal to the second longitudinal distance and second cutting member is displaced a distance less than the second longitudinal distance.

23. The method of claim 22, wherein the second cutting member is automatically decoupled from the impact member after the impact member travels a portion of the second longitudinal distance.

24. The method of claim 18, further comprising adjusting the biopsy device to control the length of tissue sample by adjusting the position of a stop member, over a continuous range, relative to the handle wherein the stop member interacts with the impact member.

25. The method of claim 24, further comprising adjusting the length of the tissue sample over range between 2 mm and 35 mm.

26. The method of claim 22, wherein the second cutting member is coupled to the follower.

* * * * *